US010248838B2

(12) United States Patent
Ozcan et al.

(10) Patent No.: US 10,248,838 B2
(45) Date of Patent: Apr. 2, 2019

(54) METHOD AND DEVICE FOR SINGLE MOLECULE IMAGING

(71) Applicant: THE REGENTS OF THE UNIVERSITY OF CALIFORNIA, Oakland, CA (US)

(72) Inventors: Aydogan Ozcan, Los Angeles, CA (US); Qingshan Wei, Los Angeles, CA (US); Wei Luo, Santa Clara, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 87 days.

(21) Appl. No.: 15/368,420

(22) Filed: Dec. 2, 2016

(65) Prior Publication Data
US 2017/0160197 A1 Jun. 8, 2017

Related U.S. Application Data

(60) Provisional application No. 62/263,089, filed on Dec. 4, 2015.

(51) Int. Cl.
*G01N 21/64* (2006.01)
*G06T 5/00* (2006.01)
(Continued)

(52) U.S. Cl.
CPC ..... *G06K 9/00134* (2013.01); *G01N 21/6456* (2013.01); *G01N 21/6458* (2013.01);
(Continued)

(58) Field of Classification Search
CPC .. G06K 9/00134; G06K 9/00127; G06K 9/00; G01N 21/64; G06T 5/00; G06T 7/00; G06T 3/60
See application file for complete search history.

(56) References Cited

U.S. PATENT DOCUMENTS 9,057,702 B2 * 6/2015 Ozcan ............... G01N 21/6486
2012/0148141 A1 6/2012 Ozcan et al.
(Continued)

OTHER PUBLICATIONS

Baday, M. et al., Multicolor super-resolution DNA imaging for genetic analysis. Nano Lett. 12, 3861-3866 (2012).
(Continued)

*Primary Examiner* — Bobbak Safaipour
(74) *Attorney, Agent, or Firm* — Vista IP Law Group LLP

(57) ABSTRACT

A device and method for imaging fluorescently labeled molecules (e.g., nucleic acids) includes securing a modular attachment device to the mobile phone with a sample containing stretched, fluorescently labeled nucleic acid molecules and illuminating the sample with excitation light to cause the fluorescently labeled nucleic acid molecules to emit fluorescent light. Images of the nucleic acids are captured using a camera of the mobile phone. The images from the mobile phone are transferred to a remote computer for image processing and analysis. The images are processed by the remote computer to generate analysis data of sample, wherein the analysis data includes the length of nucleic acid molecules contained in the sample or the length of molecular sub-region(s). The mobile phone or another computing device receives from the remote computer the analysis data and displays at least some of the analysis data thereon.

11 Claims, 14 Drawing Sheets

(51) Int. Cl.
  *G06K 9/00* (2006.01)
  *G06T 7/00* (2017.01)
  *G06T 3/60* (2006.01)
  *G06T 7/60* (2017.01)
(52) U.S. Cl.
  CPC .............. *G06T 7/60* (2013.01); *G06K 9/0014* (2013.01); *G06T 2207/10024* (2013.01); *G06T 2207/10064* (2013.01); *G06T 2207/30072* (2013.01)

(56) References Cited

U.S. PATENT DOCUMENTS

| | | |
|---|---|---|
| 2012/0157160 A1 | 6/2012 | Ozcan et al. |
| 2012/0218379 A1 | 8/2012 | Ozcan et al. |
| 2012/0248292 A1 | 10/2012 | Ozcan et al. |
| 2012/0281899 A1 | 11/2012 | Ozcan et al. |
| 2013/0092821 A1 | 4/2013 | Ozcan et al. |
| 2013/0157351 A1 | 6/2013 | Ozcan et al. |
| 2013/0193544 A1 | 8/2013 | Ozcan |
| 2013/0203043 A1 | 8/2013 | Ozcan et al. |
| 2013/0258091 A1 | 10/2013 | Ozcan et al. |
| 2013/0280752 A1 | 10/2013 | Ozcan et al. |
| 2014/0120563 A1 | 5/2014 | Ozcan et al. |
| 2014/0160236 A1 | 6/2014 | Ozcan et al. |
| 2014/0300696 A1 | 10/2014 | Ozcan et al. |
| 2015/0111201 A1 | 4/2015 | Ozcan et al. |
| 2015/0141268 A1* | 5/2015 | Rothberg ............. C12Q 1/6869 506/2 |
| 2015/0153558 A1 | 6/2015 | Ozcan et al. |
| 2015/0204773 A1 | 7/2015 | Ozcan et al. |
| 2016/0070092 A1* | 3/2016 | Ozcan ................. G02B 21/362 348/79 |
| 2016/0161409 A1 | 6/2016 | Ozcan et al. |
| 2016/0327473 A1 | 11/2016 | Ozcan et al. |
| 2016/0334614 A1 | 11/2016 | Ozcan et al. |
| 2017/0153106 A1 | 6/2017 | Ozcan et al. |
| 2017/0160197 A1 | 6/2017 | Ozcan et al. |
| 2017/0168285 A1 | 6/2017 | Ozcan et al. |
| 2017/0220000 A1 | 8/2017 | Ozcan et al. |
| 2017/0357083 A1 | 12/2017 | Ozcan et al. |
| 2018/0003686 A1 | 1/2018 | Ozcan et al. |
| 2018/0052425 A1 | 2/2018 | Ozcan et al. |
| 2018/0196193 A1 | 7/2018 | Ozcan et al. |

OTHER PUBLICATIONS

Betzig, E. et al., Imaging intracellular fluorescent proteins at nanometer resolution. Science 313, 1642-1645 (2006).
Breslauer, D.N. et al., Mobile phone based clinical microscopy for global health applications. PLoS ONE, vol. 4, Issue 7, e6320 (2009).
Chan, T.F. et al., A simple DNA stretching method for fluorescence imaging of single DNA molecules. Nucleic Acids vol. 34, No. 17, e113 (2006).
Cisse, I. et al., Fueling protein-DNA interactions inside porous nanocontainers. Proc. Natl. Acad. Sci. vol. 104, No. 31, 12646-12650 (2007).
Chou, H.P. et al., A microfabricated device for sizing and sorting DNA molecules. Proc. Natl. Acad. Sci. vol. 96, 11-13 (1999).
Coskun, A.F. et al., Albumin testing in urine using a smart-phone. Lab Chip 13, 4231-4238 (2013).
Coskun, A.F. et al., A personalized food allergen testing platform on a cellphone. Lab Chip 13, 636-640 (2013).
Feng, S. et al., Immunochromatographic diagnostic test analysis using Google Glass. ACS Nano 8, 3069-3079 (2014).
Filippini, D. et al., Chemical sensing with familiar devices. Angew. Chem. Int. Ed. 45, 3800-3803 (2006).
Gallegos, D. et al., Label-free biodetection using a smartphone. Lab Chip 13, 2124-2132 (2013).
Forget, A.L. et al., Single-molecule imaging of DNA pairing by RecA reveals a three-dimensional homology search. Nature 482, 423-427 (2012).

Greenleaf, W.J. et al., High-resolution, single-molecule measurements of biomolecular motion. Annu. Rev. Biophys. Biomol. Struct. 36, 171-190 (2007).
Ha, T. et al., Single molecule dynamics studied by polarization modulation. Phys. Rev. Lett. 77, 3979-3982 (1996).
Harris, T.D. et al., Single-molecule DNA sequencing of a viral genome. Science 320, 106-109 (2008).
Haun, J.B. et al., Micro-NMR for rapid molecular analysis of human tumor samples. Sci. Transl. Med. 3, 71ra16 (2011).
Herrick, J. et al., Quantifying single gene copy number by measuring fluorescent probe lengths on combed genomic DNA. Proc. Natl. Acad. Sci. USA 97, 222-227 (2000).
Lee, J.A. et al., Genomic rearrangements and gene copy-number alterations as a cause of nervous system disorders. Neuron 52, 103-121 (2006).
Ludwig, S.J. et al., Cellphone-based detection platform for rbST biomarker analysis in milk extracts using a microsphere fluorescence immunoassay. Anal. Bioanal. Chem. DOI: 10.1007/s00216-014-7984-4 (2014).
Martinez, A.W., et al., Diagnostics for the developing world: microfluidic paper-based analytical devices. Anal. Chem. 82, 3-10 (2009).
Moerner, W.E., New directions in single-molecule imaging and analysis. Proc. Natl. Acad. Sci. USA 104, 12596-12602 (2007).
Mudanyali, O. et al., Integrated rapid-diagnostic-test reader platform on a cellphone. Lab Chip 12, 2678-2686 (2012).
Oncescu, V. et al., Cholesterol testing on a smartphone. Lab Chip 14, 759-763 (2014).
Oncescu, V. et al., Smartphone based health accessory for colorimetric detection of biomarkers in sweat and saliva. Lab Chip 13, 3232-3238 (2013).
Ozcan, A., Mobile phones democratize and cultivate next-generation imaging, diagnostics and measurement tools. Lab Chip 14, 3187-3194 (2014).
Ozcan, A., Educational games for malaria diagnosis. Sci. Transl. Med. 6, 233 ed239 (2014).
Pamplona, V.F. et al., NETRA: Interactive Display for Estimating Refractive Errors and Focal Range, ACM Transactions on Graphics, vol. 29, 77 (2010).
Pertsinidis, A. et al., Subnanometre single-molecule localization, registration and distance measurements. Nature 466, 647-651 (2010).
Price, R.N. et al., Mefloquine resistance in Plasmodium falciparum and increased pfmdr1 gene copy number. Lancet 364, 438-447 (2004).
Ray, M. et al., Discovery of structural alterations in solid tumor oligodendroglioma by single molecule analysis. BMC Genomics 14, 505 (2013).
Rust, M.J., et al., Sub-diffraction-limit imaging by stochastic optical reconstruction microscopy (STORM). Nat. Methods 3, 793-796 (2006).
Shen, L., et al., Point-of-care colorimetric detection with a smartphone. Lab Chip 12, 4240-4243 (2012).
Sidorova, J.M. et al., Microfluidic-assisted analysis of replicating DNA molecules. Nat. Protocols 4, 849-861 (2009).
Seisenberger, G. et al., Real-time single-molecule imaging of the infection pathway of an adeno-associated virus. Science 294, 1929-1932 (2001).
Smith, Z.J. et al., Nanometer-scale sizing accuracy of particle suspensions on an unmodified cell phone using elastic light scattering. PLoS ONE 7, e46030 (2012).
Schwartz, J.J. et al., Single molecule measurement of the "speed limit" of DNA polymerase. Proc. Natl. Acad. Sci. USA 106, 20294-20299 (2009).
Stankiewicz, P. et al., J.R. Structural variation in the human genome and its role in disease. Annu. Rev. Med. 61, 437-455 (2010).
Teague, B. et al., High-resolution human genome structure by single-molecule analysis. Proc. Natl. Acad. Sci. USA 107, 10848-10853 (2010).
Tokunaga, M. et al., Highly inclined thin illumination enables clear single-molecule imaging in cells. Nat. Methods 5, 159-161 (2008).
Vashist, S. et al., A. Cellphone-based devices for bioanalytical sciences. Anal. Bioanal. Chem. 406, 3263-3277 (2014).

(56) References Cited

OTHER PUBLICATIONS

Wei, Q. et al., Fluorescent imaging of single nanoparticles and viruses on a smart phone. ACS Nano 7, 9147-9155 (2013).
Wei, Q. et al., Detection and spatial mapping of mercury contamination in water samples using a smart-phone. ACS Nano 8, 1121-1129 (2014).
Won, B.Y. et al., A touchscreen as a biomolecule detection platform. Angew. Chem. Int. Ed. 51, 748-751 (2012).
Yildiz, A. et al., Myosin V walks hand-over-hand: single fluorophore imaging with 1.5-nm localization. Science 300, 2061-2065 (2003).
Yu, H. et al., Plasmonic imaging and detection of single DNA molecules. ACS Nano 8, 3427-3433 (2014).
Zhu, H. et al., Quantum dot enabled detection of *Escherichia coli* using a cell-phone. Analyst 137, 2541-2544 (2012).
Zhu, H. et al., Cost-effective and rapid blood analysis on a cell-phone. Lab Chip 13, 1282-1288 (2013).
Zhu, H. et al., Optofluidic fluorescent imaging cytometry on a cell phone. Anal. Chem. 83, 6641-6647 (2011).
Wei et al., Imaging and Sizing of Single DNA Molecules on a Mobile Phone, ACS Nano, vol. 8, No. 12, pp. 12725-12733 (Dec. 10, 2014).

\* cited by examiner

Front · Back

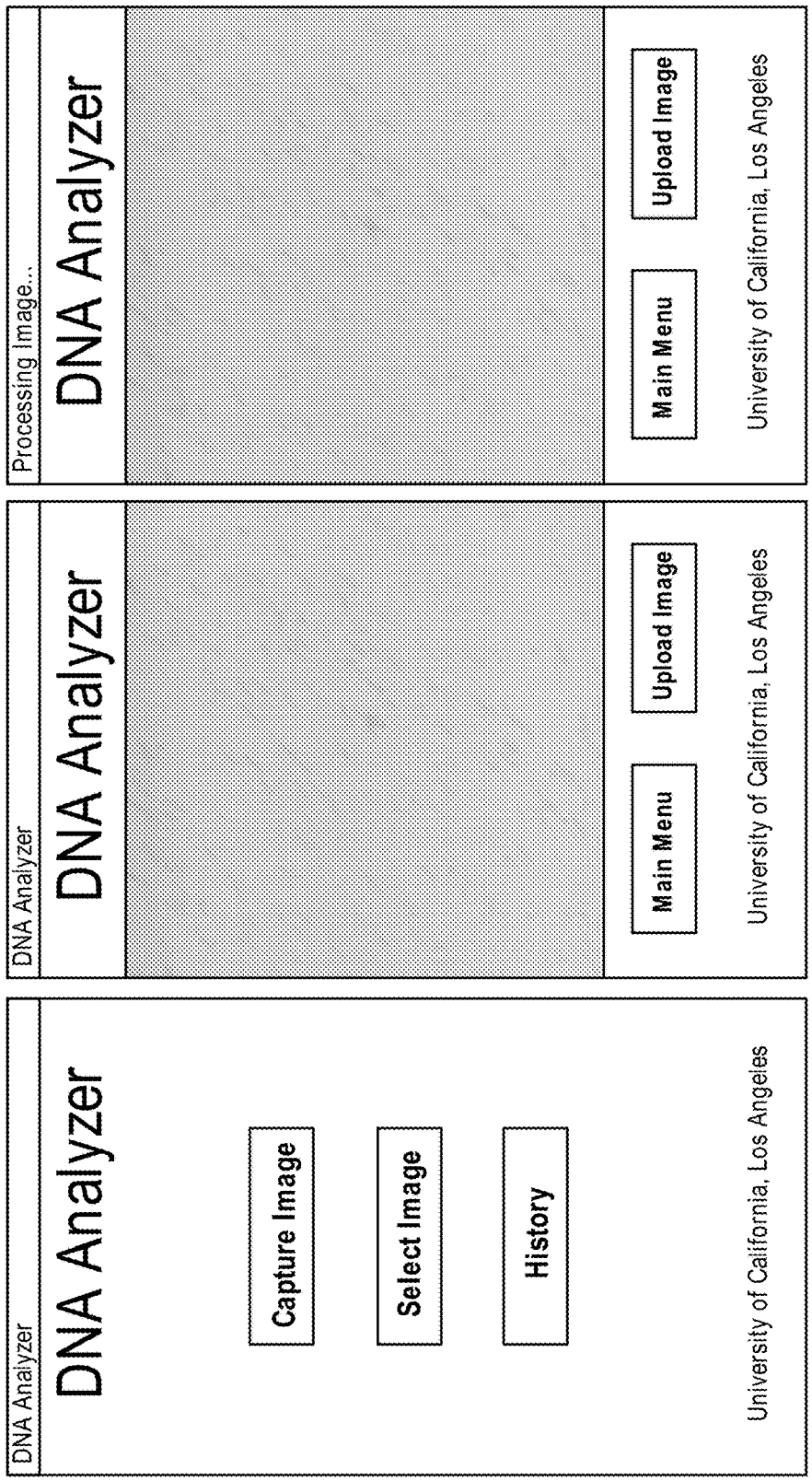

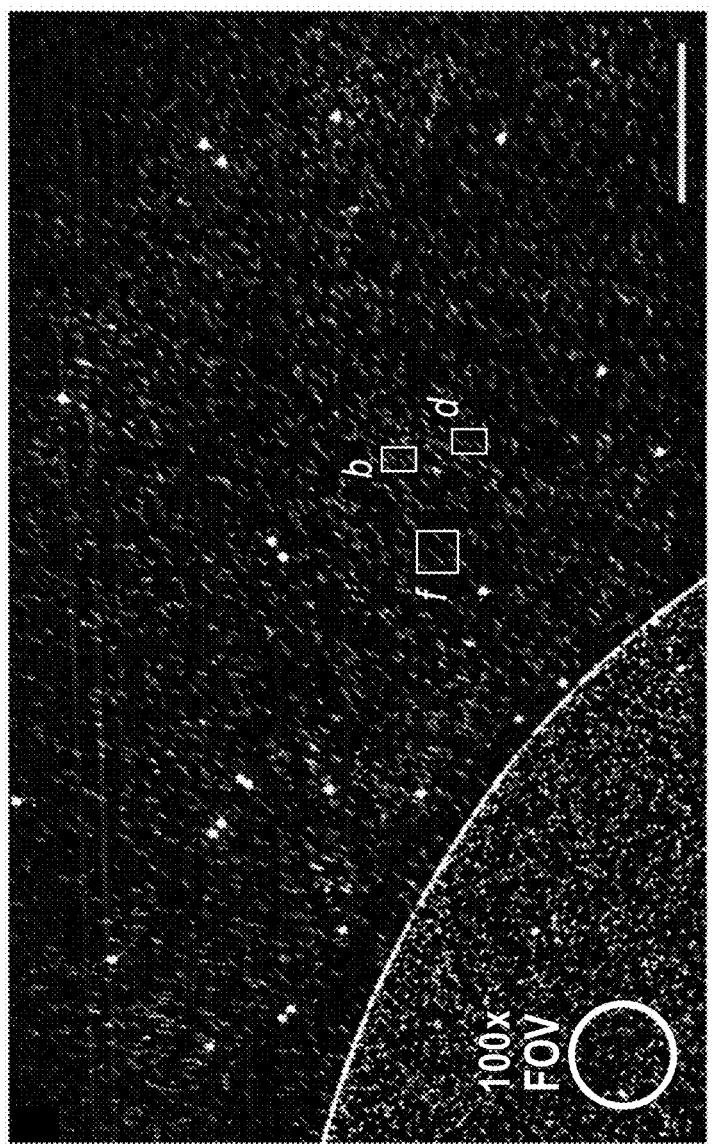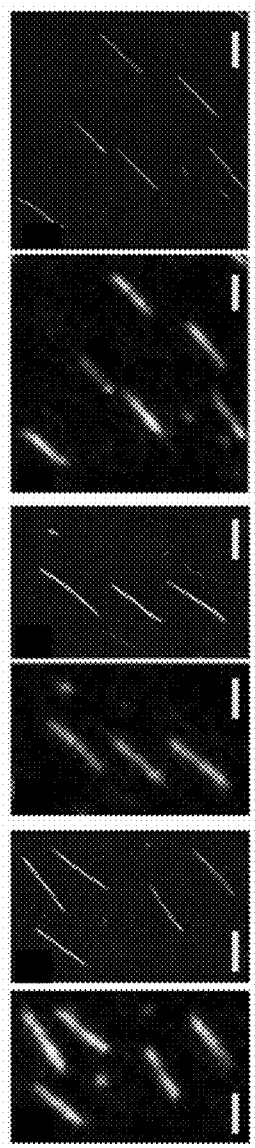

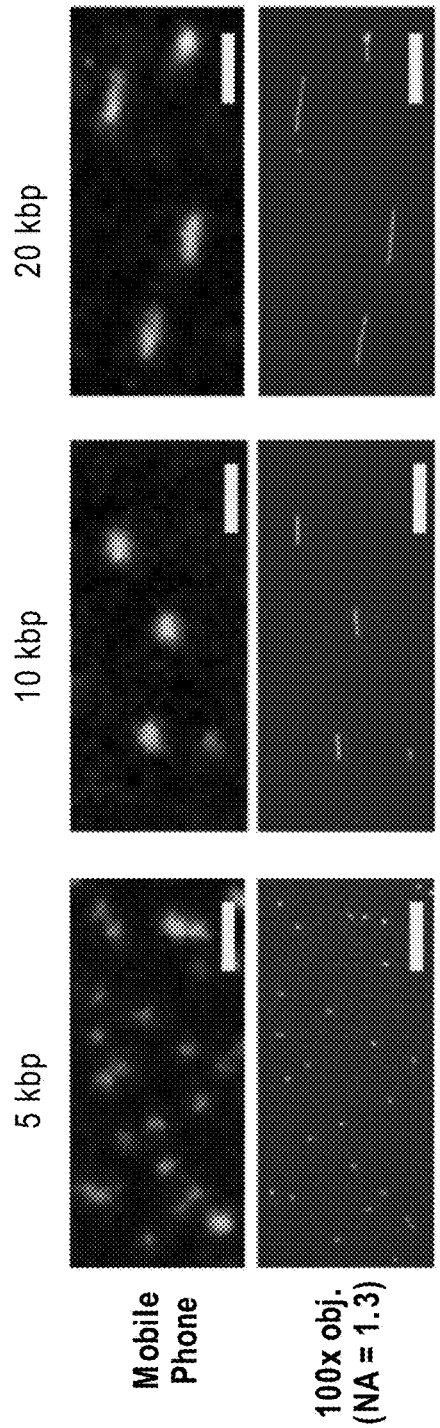
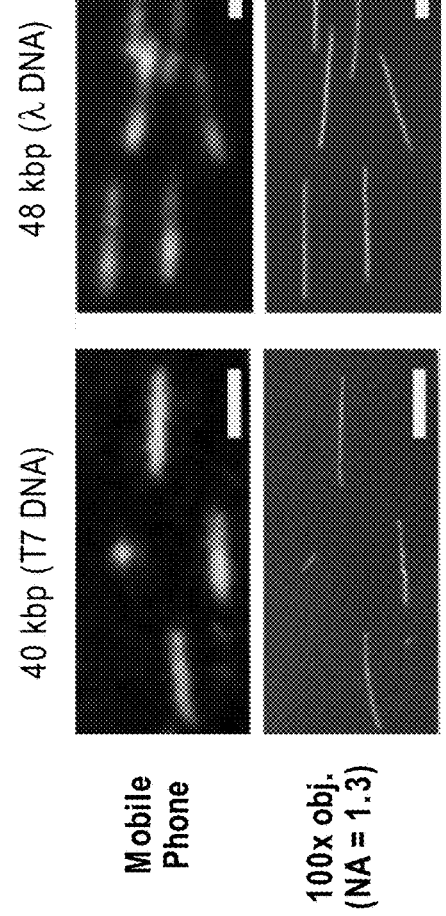
FIG. 6A  FIG. 6B  FIG. 6C  FIG. 6D  FIG. 6E

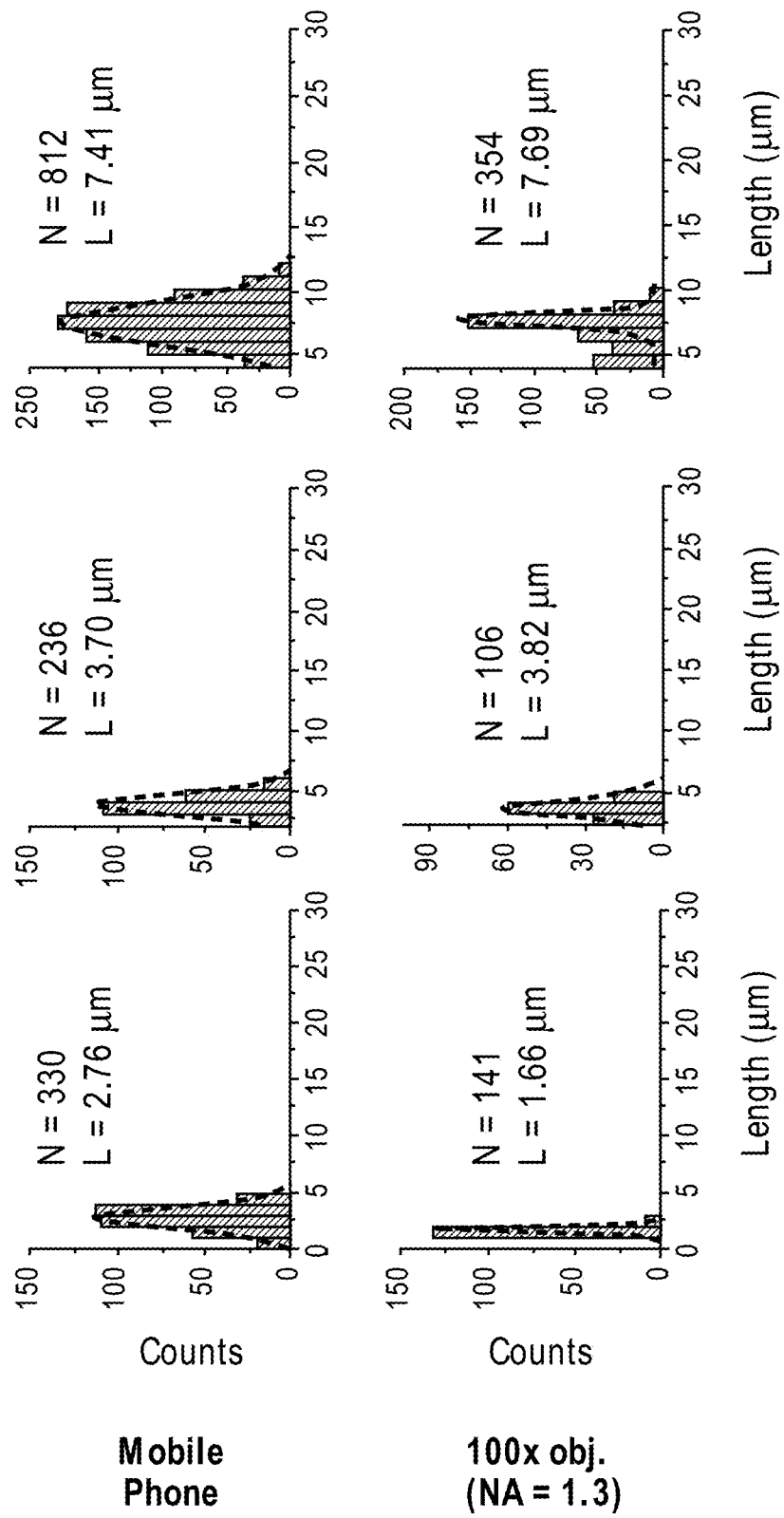

FIG. 9A
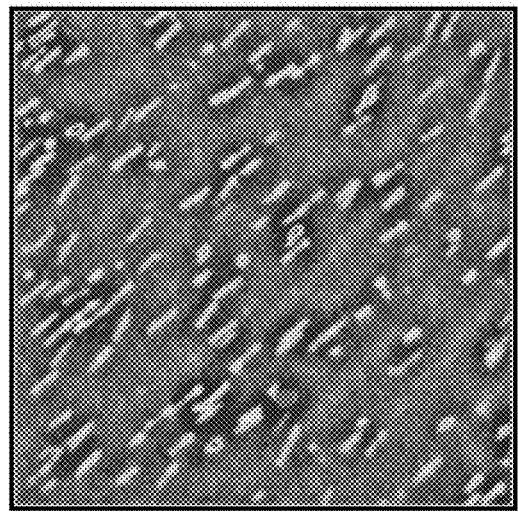
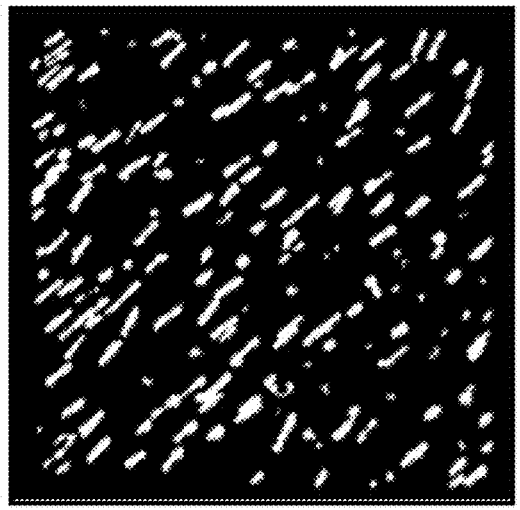
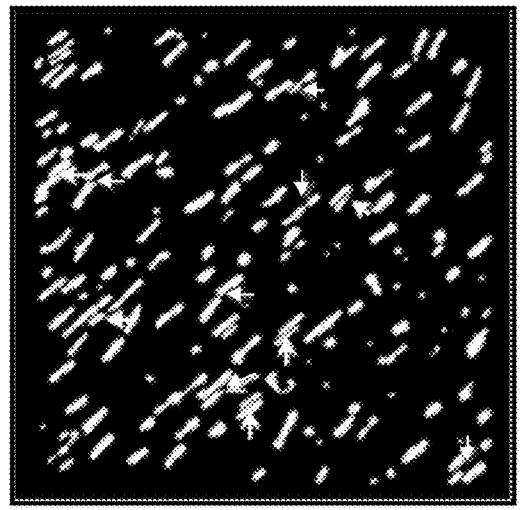
FIG. 9B      FIG. 9C

METHOD AND DEVICE FOR SINGLE MOLECULE IMAGING

RELATED APPLICATION

This application claims priority to U.S. Provisional Patent Application No. 62/263,089 filed on Dec. 4, 2015, which is hereby incorporated by reference in its entirety. Priority is claimed pursuant to 35 U.S.C. § 119 and any other applicable statute.

STATEMENT REGARDING FEDERALLY SPONSORED RESEARCH AND DEVELOPMENT

This invention was made with government support under Grant Number 1444240, awarded by the National Science Foundation. The government has certain rights in the invention.

TECHNICAL FIELD

The technical field generally relates to imaging methods and devices and more specifically to methods and devices for imaging and measuring single molecules and in particular nucleic acids (e.g., DNA).

BACKGROUND

Optical methods for imaging single biomolecules allow for exploration of their individual behavior and properties at the nanoscale level, which not only significantly advances knowledge of molecular biology and biophysics but also provide various diagnostics opportunities for biomedical applications. Imaging of single DNA molecules has been of particular interest as various diseases including cancer and neurological disorders such as Alzheimer's disease are associated with genomic alterations, including for example copy-number variations (CNVs). High spatial resolution and nondestructive nature of optical imaging methods are especially attractive for probing DNA-protein interactions or mapping genetic information from individual DNA molecules. These research and development efforts, however, have been mostly limited to advanced laboratory facilities using relatively costly, complex and bulky imaging set-ups, including for example confocal fluorescence microscopy, super-resolution microscopy, or label-free plasmonic imaging. Translation of these and other existing imaging techniques to field-portable, cost-effective and high-throughput instruments would open up a myriad of new applications in e.g., point-of-care (POC) medicine, global health and diagnostics fields, among others, and would also positively impact research and educational efforts in developing countries and resource-limited institutions, helping the democratization of advanced scientific instruments and measurement tools. To this end, mobile phones and other consumer electronics devices, including e.g., tablet PCs and wearable computers, have been emerging as powerful platforms to create cost-effective, portable and readily accessible alternatives to some of the advanced biomedical imaging and measurement tools. Mobile phones in particular have been experiencing significant advances in their optical imaging hardware, approximately doubling their space-bandwidth product every two years over the last ~10-15 years, recently reaching to more than 40 million pixels in mobile phone-based digital camera systems. In addition to advanced optical interfaces that are now used in mobile phones, the computational power (now also including Graphics Processing Units, GPUs), data connectivity, massive volume (with >7 billion subscribers) and cost-effectiveness of mobile phones make them an ideal platform for conducting various advanced biomedical experiments and tests, including e.g., blood analysis, measurement of analytes in bodily fluids, flow-cytometry, among various others.

Despite all of these recent advances and progress, imaging of single DNA molecules on a mobile phone device has not be achieved, leaving it as one of the major remaining milestones in mobile phone based imaging and microanalysis systems, mostly due to extremely weak signal-to-noise ratio (SNR) and limited contrast of single molecule samples in the optical portion of the electro-magnetic spectrum.

SUMMARY

In one embodiment, a mobile phone-based device for the imaging and length quantification of individual nucleic acid molecules (e.g., DNA) is demonstrated. The device uses a field-portable and cost-effective modular attachment device that is mountable on the housing or body of the mobile phone device. The modular attachment device is mounted to align or integrate with the existing camera of the mobile phone. This modular attachment device, which in some embodiments weighs less than 190 grams (including three AAA batteries), utilizes a compact laser-diode (e.g., 450 nm, 75 mW) to excite fluorescently labeled molecules at a high-incidence angle of ~75°. The optical path in the modular attachment device includes a thin-film based interference filter located therein to create a very strong dark-field performance; significantly suppressing the background noise created by the high-power excitation beam.

The modular attachment device, in one embodiment, contains a miniature dovetail stage for depth-of-focus adjustment and a lens (or set of lenses) that is used to form a magnified image of the fluorescent specimen onto the imaging sensor or imaging chip of the mobile phone. The mobile phone includes software or an application "app" that is has a user interface that guides a user through the process operations needed to image single molecules. The user interface also provides a communication platform to transfer the raw images with a custom-designed back-end server that runs software thereon for digital processing of the acquired fluorescent images to rapidly quantify the length of each single molecule or specific sub-regions of the nucleic acid molecules. In one embodiment where the molecule is a nucleic acid strand, the measured fluorescent signatures of the stretched nucleic acid strand is fitted to the mobile phone microscope's two-dimensional (2D) point-spread-function (PSF). The results of the single molecule detection and length measurement process can be visualized on the screen of the mobile phone and, optionally, also through one or more remote computing devices.

In one embodiment, a method for imaging and sizing fluorescently labeled nucleic acid molecules using a mobile phone includes securing a modular attachment device to the mobile phone with a sample containing stretched, fluorescently labeled nucleic acid molecules. The sample is illuminated with excitation light to cause the fluorescently labeled nucleic acids to emit fluorescent light. One or more images of the fluorescently labeled nucleic acids in the sample are captured using a camera of the mobile phone. The one or more images from the mobile phone are transmitted to a remote computer having at least one processor for image processing and analysis. The one or more images are processed with the at least one processor of the remote computer to generate analysis data of sample, wherein the analysis data includes the lengths of individual nucleic acid molecules or the lengths of specific sub-regions of nucleic acid molecules contained in the sample. The analysis data is received from the remote computer and at least some of the analysis data is displayed on a display of the mobile phone, a laptop, personal computer, or tablet computing device.

In another embodiment, a method for imaging and sizing fluorescently labeled nucleic acid molecules using a mobile phone includes securing a modular attachment device to the mobile phone with a sample containing stretched, fluorescently labeled nucleic acid molecules. The sample is illuminated with excitation light to cause the fluorescently labeled nucleic acid molecules to emit fluorescent light. One or more images of the fluorescently labeled nucleic acid molecules in the sample are captured using a camera of the mobile phone. The one or more images are processed with at least one processor of the mobile phone to generate analysis data of sample, wherein the analysis data includes the length of nucleic acid molecules or specific sub-regions of nucleic acid molecules contained in the sample. The analysis data is displayed on a display of the mobile phone.

In another embodiment, a device or system for imaging fluorescently labeled nucleic acid molecules in a sample includes a mobile phone having a camera therein. The device or system includes a modular attachment device configured to mount to the mobile phone and position a fluorescently labeled nucleic acid sample contained therein within a field of view of the camera. The modular attachment device includes an excitation light source; a sample holder configured to hold the sample containing the fluorescently labeled nucleic acid compressed between two optically transparent substrates, wherein fluorescently labeled nucleic acid molecules are stretched or extended in response to a compression force applied to the two optically transparent substrates; a lens or set of lenses for magnifying the image of the sample; a filter interposed between the lens and the camera of the mobile phone and configured to reject scattered background light from the excitation light source and transmit fluorescent light through the filter; and a moveable stage for moving the excitation light source and sample holder relative to the camera of the mobile phone. The mobile phone includes software or an application executed thereon to identify molecules of fluorescently labeled nucleic acid in the sample along with their respective lengths or lengths of sub-regions of the nucleic acid molecules.

BRIEF DESCRIPTION OF THE DRAWINGS

FIGS. 3A-3F illustrate screenshot images illustrating the GUI of the software application running on the mobile phone that is used to acquire images and upload the same to a remote server for processing. Results are returned to the mobile phone where they are displayed to the user on the GUI.

FIG. 4A illustrates a large field-of-view (FOV) (~2 mm$^2$) mobile phone image of labeled DNA molecules stretched on a glass substrate. This image is taken at the boundary of the initial DNA droplet placed on the substrate, and it is averaged using thirteen (13) successive mobile phone images and is displayed after background subtraction. The inset (circle) shows a typical FOV corresponding to a 100× objective-lens. The large circular-shaped fluorescent spots that appear in this image are 500 nm green fluorescent polystyrene beads which are added into the sample to assist depth focusing and location matching (for comparison purposes). Scale bar=250 µm.

FIG. 4B illustrates an enlarged mobile phone image showing single DNA molecules within the box labeled "b" in FIG. 4A.

FIG. 4C illustrates the corresponding conventional bench-top fluorescence microscope image of the same molecules in region "b" of FIG. 4B obtained using a 100× oil-immersion objective lens (NA=1.3) and a cooled monochrome CCD camera. Scale bar=10 µm.

FIG. 4D illustrates an enlarged mobile phone image showing single DNA molecules within the box labeled "d" in FIG. 4A.

FIG. 4E illustrates the corresponding conventional bench-top fluorescence microscope image of the same molecules in region "d" of FIG. 4D obtained using a 100× oil-immersion objective lens (NA=1.3) and a cooled monochrome CCD camera. Scale bar=10 µm.

FIG. 4F illustrates an enlarged mobile phone image showing single DNA molecules within the box labeled "f" in FIG. 4A.

FIG. 4G illustrates the corresponding conventional bench-top fluorescence microscope image of the same molecules in region "f" of FIG. 4F obtained using a 100× oil-immersion objective lens (NA=1.3) and a cooled monochrome CCD camera. Scale bar=10 µm.

FIG. 6A illustrates an image obtained of a 5 kbp segment of DNA with the mobile phone based microscope platform (top) along with a comparison image (bottom) of the same segment of DNA obtained using a bench-top fluorescence microscope.

FIG. 6B illustrates an image obtained of a 10 kbp segment of DNA with the mobile phone based microscope platform (top) along with a comparison image (bottom) of the same segment of DNA obtained using a bench-top fluorescence microscope.

FIG. 6C illustrates an image obtained of a 20 kbp segment of DNA with the mobile phone based microscope platform (top) along with a comparison image (bottom) of the same segment of DNA obtained using a bench-top fluorescence microscope.

FIG. 6D illustrates an image obtained of a 40 kbp segment of T7 DNA with the mobile phone based microscope platform (top) along with a comparison image (bottom) of the same segment of DNA obtained using a bench-top fluorescence microscope.

FIG. 6E illustrates an image obtained of a 48 kbp segment of λ DNA with the mobile phone based microscope platform (top) along with a comparison image (bottom) of the same segment of DNA obtained using a bench-top fluorescence microscope.

FIG. 7A illustrates a histogram of measured lengths for a 5 kbp segment of DNA using the mobile phone based microscope platform (top) along with histogram measurements obtained using a bench-top fluorescence microscope (NA=1.3) (bottom).

FIG. 7B illustrates a histogram of measured lengths for a 10 kbp segment of DNA using the mobile phone based microscope platform (top) along with histogram measurements obtained using a bench-top fluorescence microscope (NA=1.3) (bottom).

FIG. 7C illustrates a histogram of measured lengths for a 20 kbp segment of DNA using the mobile phone based microscope platform (top) along with histogram measurements obtained using a bench-top fluorescence microscope (NA=1.3) (bottom).

FIG. 9A illustrates a representative fluorescent image of λ DNA (RGB color scale) obtained using the mobile phone and modular attachment device.

FIG. 9B illustrates a preliminary object mask generated by using an intensity threshold.

FIG. 9C illustrates an improved object mask that uses curvature detection algorithm to digitally separate end-to-end conjugated DNA masks (darker arrows) and side-by-side conjugated DNA masks (lighter arrows).

DETAILED DESCRIPTION OF THE ILLUSTRATED EMBODIMENTS

Figure 1A:
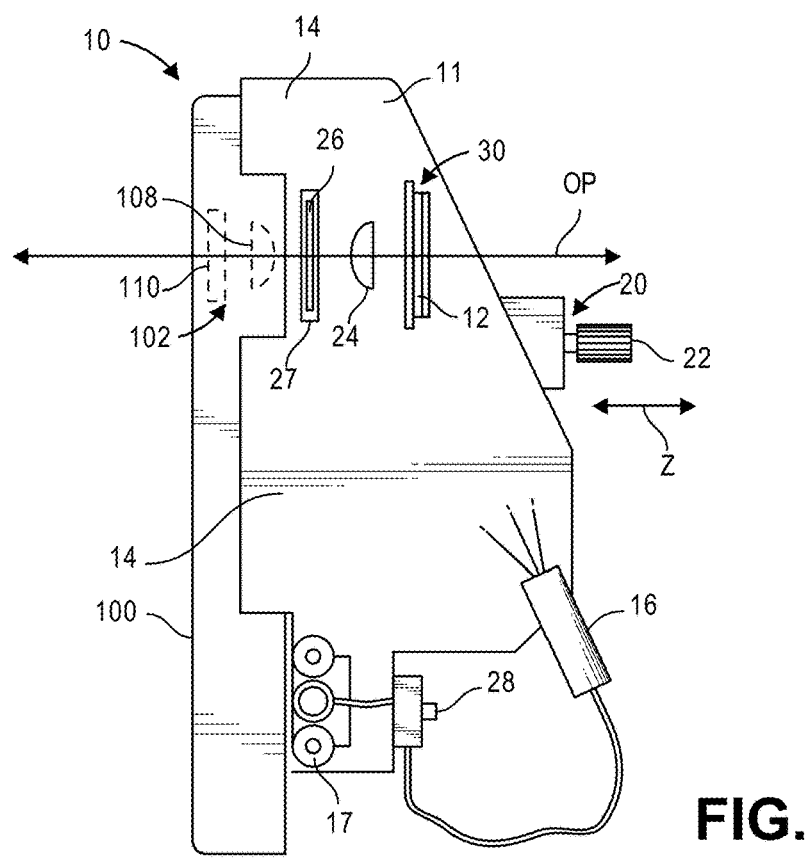
FIG. 1A illustrates a side view of a modular attachment device configured to mount to the mobile phone. The side of the modular attachment device is cut away to illustrate inner components.
Figure 1B:
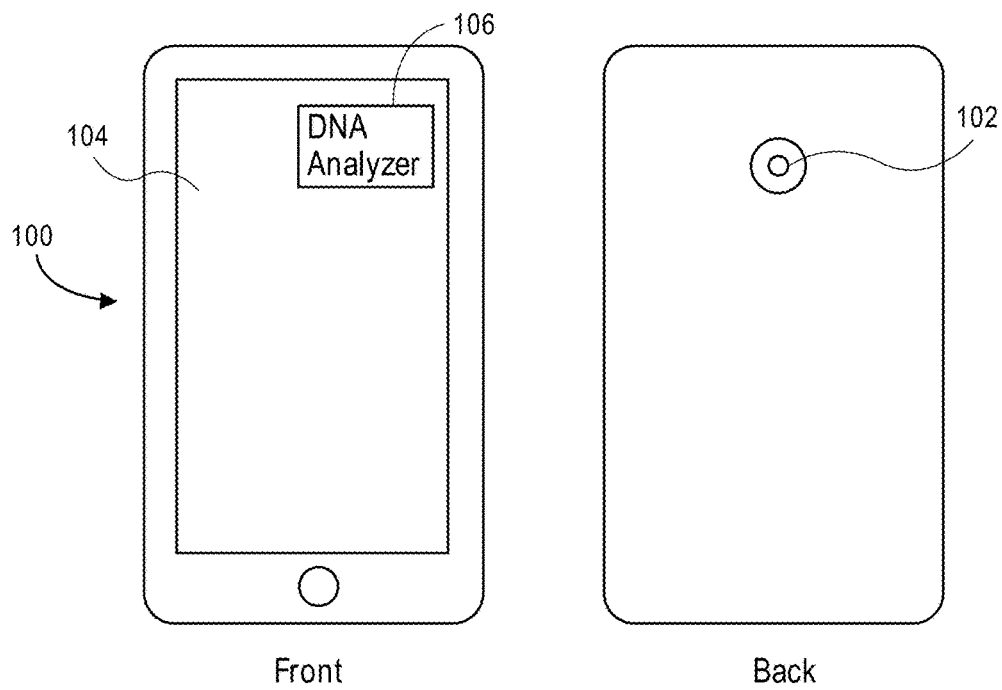
FIG. 1B illustrates front and back views of a mobile phone device according to one embodiment.
Figure 1C:
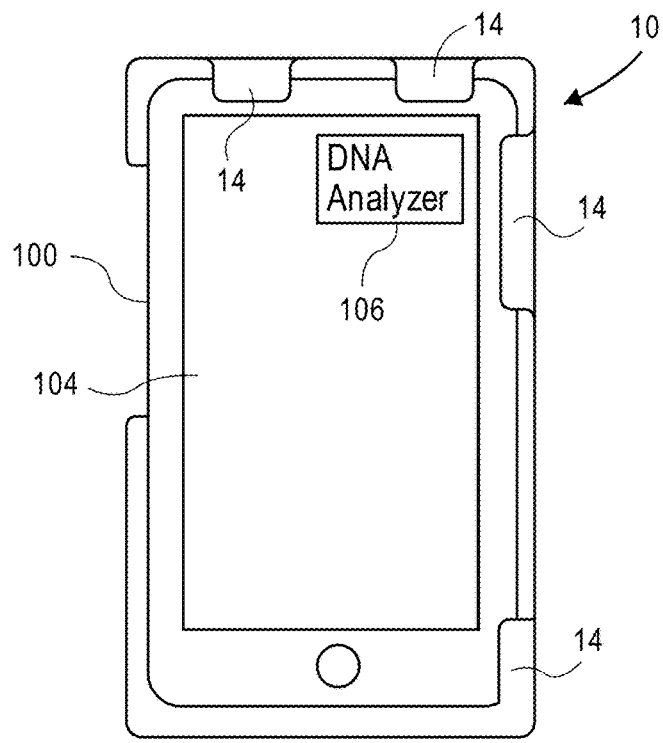
FIG. 1C illustrates a schematic illustration of the modular attachment device mounted on a mobile phone. The screen or display of the mobile phone illustrates the graphical user interface (GUI) of software or an application for analyzing single molecules (e.g., nucleic acids).

FIG. 1A illustrates a modular attachment device 10 that is used in conjunction with a mobile phone 100 as also seen in FIGS. 1B and 1C for single molecule imaging and sizing. The mobile phone 100 may include any number of makes and models of mobile phones. The mobile phone 100 includes a camera 102 that is used to obtain images of a sample 12 containing the molecules to be imaged when mounted to the modular attachment device 10. The mobile phone 100 includes a display or screen 104 that is used by the user to display information and interact with the mobile phone 100. The mobile phone 100 includes an application or software 106 that is loaded or otherwise executable by the mobile phone 100. The software 106 is used to acquire images of the sample 12 using the modular attachment device 10. In one embodiment, the software 106 may be downloaded from a website or "store" as is typically used with software or applications that run on mobile phones 100. The software 106 provides a graphical user interface (GUI) through which the user interacts with to acquire images of a sample 12 as well as view automatically generated data regarding sizing of molecules within the sample 12 as explained herein.

The modular attachment device 10 is made to temporarily secure itself to the side of the mobile phone 100 that contains the camera 102. In the embodiment illustrated in FIG. 1A, the modular attachment device 10 is secured to back side of the mobile phone 100 so that an optical path (OP) is created between a sample 12 that is contained in a sample holder 30 that is located inside the modular attachment device 10 and the camera 102. The camera 102 of the mobile phone 100 typically includes a lens 108 that is positioned adjacent to an image sensor 110 or imaging chip that is contained within the camera 100. The image sensor 110 or imaging chip may include a CCD or CMOS image sensor. Typically, the image sensor 110 or imaging chip is a color-based sensor that is capable of acquiring color images.

The modular attachment device 10 can be temporarily secured to the housing or body of the mobile phone 100 using one or more clips or tabs 14 that are formed in the modular attachment device 10 as seen in FIG. 1C. The clips or tabs 14 may be flexible or bendable such that the modular attachment device 100 may be easily attached or remoted from the mobile phone 100. The dimensions of the modular attachment device 10 may vary depending on the make or model of the mobile phone 100. For example, different versions or models of the modular attachment device 10 may be made to accommodate different and shapes of mobile phones 100. In the experiments described herein, a Lumia 1020, Nokia mobile phone 100 was used. The camera lens 108 has a focal length of 6.5 mm (f=6.5 mm). The modular attachment device 10 may include a housing 11 that is used to contain the various components of the imaging device as well as the sample 12. The housing 11 may be made of a polymer material such as a plastic-based material. The housing 11 may be made using any known manufacturing techniques including 3D printing techniques.

With reference to FIG. 1A, the modular attachment device 10 includes a light source 16 that is used as an excitation light source for fluorescent probes or labels that are present within the sample 12. In one embodiment, the light source 16 is at least one laser diode (e.g., a 450 nm laser diode) that is powered by driver circuitry contained within the modular attachment device 10 and powered by one or batteries 17 that are also contained in the modular attachment device 10 and are used to power the light source 16. The light source 16 may also include a light emitting diode (LEDs) or an array of the same. The light source 16 is positioned within the modular attachment device 10 to illuminate the sample 12 at an angle of around 75° (with respect to a normal of the camera 102 along optical path OP). The laser diode light source 16 emits a laser beam that is focused through a small convex lens (not shown) (f=35 mm) to form a tight illumination spot on the sample holder 30. In the embodiment used in the experiments described herein, the average illumination power density at the sample plane was estimated to be 2.4 W/cm$^2$. To dissipate the heat, the laser diode light source 16 was mounted on a $\Phi$12×30 mm copper host and further surrounded by a $\Phi$18×40 mm aluminum heat sink. In some embodiments, these may not be needed. The modular attachment device 10 further included an adjustable stage 20 (e.g., miniature dovetail stage (DT12, Thorlabs)) that is used to move both the sample 12 (via a sample holder 30 described below) and the light source 16 (in the z direction as seen in FIG. 1A along the optical path formed between the sample 12 and the camera 102). Movement of the adjustable stage 20 controls focus of the image that is obtained by the mobile phone 100. A knob 22 can be used to adjust the movement of the stage 20 and thus the focus of the device. The focus of the modular attachment device 10 is set using the knob 22 and is generally adjusted to produce infinity focus for both PSF acquisition (using fluorescent beads) and experiments. The modular attachment device 10 further includes an external lens 24 (f=4 mm) that is used to collect fluorescent signal emitted from the sample 12. Alternatively a set of lenses 24 may be located in the modular attachment device 10 for magnification. One or more filters 26 loaded in a filter holder 27 are used to permit the passage of fluorescent light emitted from a specimen in the sample while preventing transmission of scattered excitation light. The filter holder 27 can be moveable in and out of the modular attachment device 10 such that different filters 26 can be loaded into the filter holder 27 as needed. In one embodiment, this may include two (2) stacked 500 nm longpass filters (FF01-500/LP-23.3-D, Semrock) that were placed between the external lens 24 and the mobile phone camera lens 108 to reject the scattered background light due to high-power laser excitation. As seen in FIG. 1A, the modular attachment device 10 includes a switch 28 that is used to turn the light source 16 on or off.

The modular attachment device 10 when used with the mobile phone 100 enables imaging of fluorescently labeled molecules such as nucleic acid over a large field of view. For example, as described herein, the DNA samples are imaged within a field of view that is around 2 mm$^2$ in size which is much larger than the FOV of a 100× objective lens as seen in FIG. 4A.

Figure 1D:
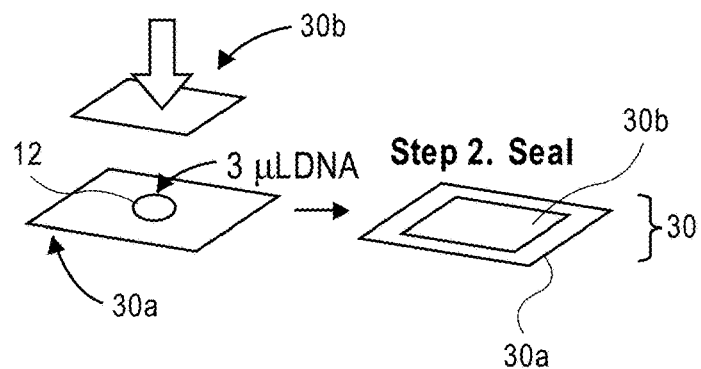
FIG. 1D illustrates a sample holder and two step method for imparting mechanical shear forces on a pre-stained or pre-dyed sample to stretch or elongate the molecules prior to imaging.

The sample 12 is contained in a sample holder 30 as seen in FIG. 1D which is loaded into the modular attachment device 10. In one aspect the sample holder 30 is used to impart shear stress on the sample 12 so as to stretch the molecules contained therein. In one particular example, the sample contains nucleic acid molecules (e.g., DNA) that are labeled with a fluorescent dye or label. In some embodiments, the entire length of the nucleic acid molecule or fragment thereof may be labelled. In other embodiments, a specific sub-region or multiple sub-regions of the nucleic acid molecule may be labelled. For example, a sub-region defining a specific gene or allele can be labeled and imaged. The fluorescent dye or label may emit light at any number of colors or wavelengths depending on the particular dye or label that is used. In the experiments described herein, a fluorescent dye or label was used that emits green colored light although other colored dyes can be used.

The sample holder 30 may include a first optically transparent substrate 30a such as a silanized glass coverslip onto which the sample 12 containing pre-stained or pre-dyed molecules are placed. A second optically transparent substrate 30b (e.g., plasma treated glass) is placed on top of the first substrate 30a. The top or second optically transparent substrate 30b is then quickly pressed down towards the first optically transparent substrate 30a (e.g., using a tweezer or the like). The droplet containing the stained nucleic acid is pushed from the center of the first substrate 30a to the edges located between the first and second substrates 30a, 30b, forming a strong shearing flow, which stretches the nucleic acid molecules on the first substrate 30a. As seen in FIG. 1D, the sample holder 30 is then sealed at the edges with a colorless adhesive (e.g., nail polish) and can be placed inside the modular attachment device 10 for imaging.

Figure 1E:
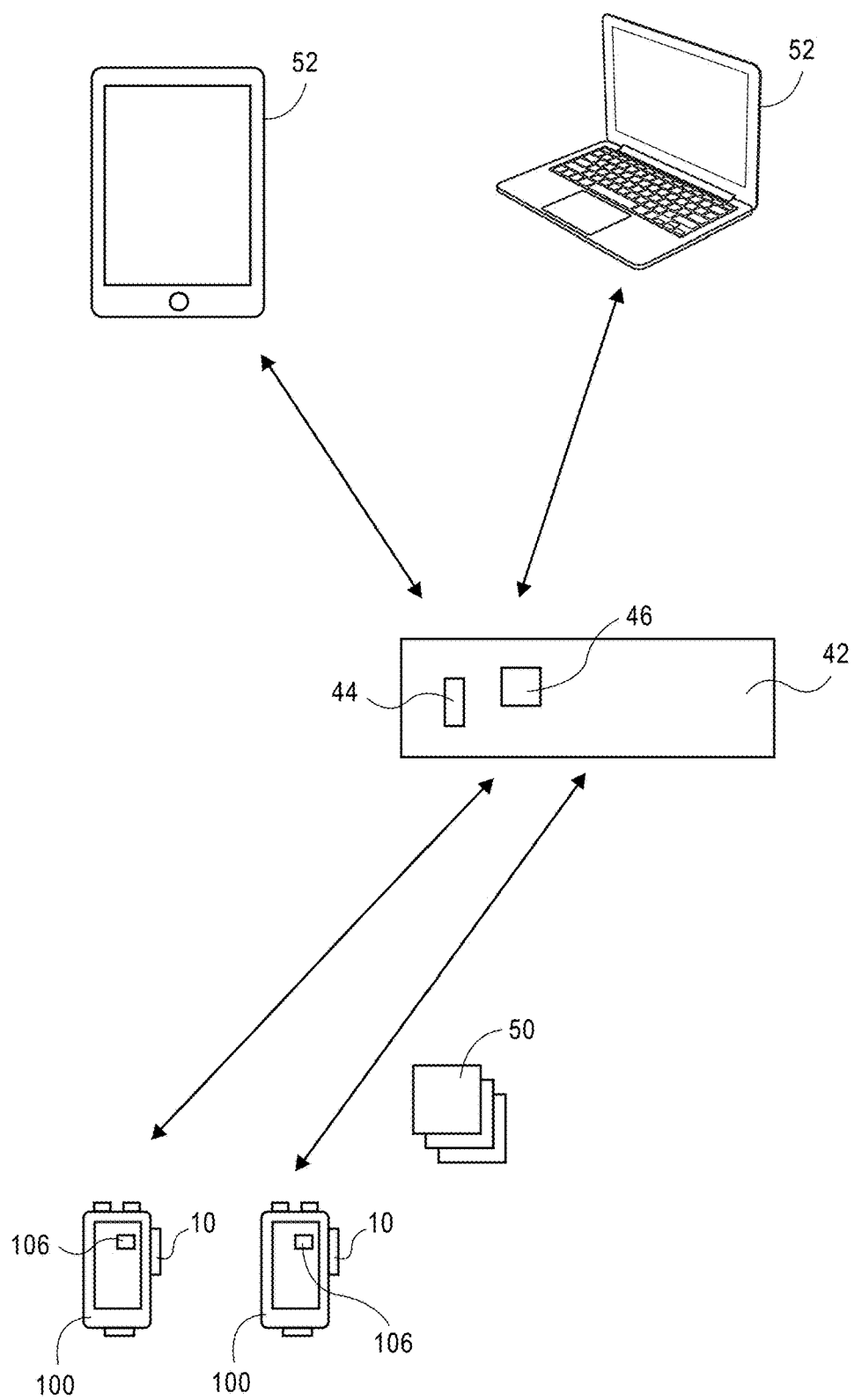
FIG. 1E illustrates a schematic representation of a system used to analyze the sizing of single molecules using the mobile phone and modular attachment device of FIGS. 1A and 1B. In this embodiment, a remote computer (e.g., server) is used to perform image processing and analysis to determine the length of molecules of nucleic acid.

FIG. 1E illustrates a schematic representation of one embodiment of a system 40 used to analyze the sizing of single molecules using the mobile phone 100 and modular attachment device 10 of FIGS. 1A-1C. In this embodiment, the system 40 includes one or more mobile phones 100 that include modular attachment devices 10 that are secured thereto to image samples 12. In this embodiment, a remote computer 42 such as a remote server is used to perform image processing and analysis on image files 50 obtained using the mobile phones 100. The remote computer 42 contains one or more processors 44 therein that execute software 46 loaded or otherwise executed by the remote computer 42 to process and analyze images files 50 that are transferred to the remote computer 42 by the mobile phone(s) 100. Files may be transferred to the remote computer 42 via a wireless network on which the mobile phones 100 operate. Files may also be transferred using a WiFi or other connection that links the mobile phone 100 to a wide area network such as the Internet.

Using the software or application 106 contained on the mobile phone 100, a user is able to upload an image 50 of the sample 12 to the remote computer 42. The image 50 that is transferred may be an image 50 of the sample 12 that has just been acquired or it may be a previously saved image 50 that is stored on the mobile phone 100. The image 50 file type may include any number of file types commonly used by mobile phones 100. On particular example is DNG format which can later be converted to TIFF format at the remote computer 42 as described herein. The image is uploaded to the remote computer 42 using HTTP for rapid digital processing by the software 46. Using the software 46 on the remote computer 42, the software rapidly quantifies the length of the molecules in the sample 12 (e.g., each strand of nucleic acid) by fitting the mobile phone's two dimensional (2D) point-spread-function (PSF) (obtained by measuring fluorescent beads or other particles) to the measured fluorescent signatures contained in the images 50. The results of the analysis can then be transferred back to the mobile phone 100 where the results can be displayed to the user on the display 104 of the mobile phone 100 using the graphical user interface of the mobile software or application 106.

Still referring to FIG. 1E, one or more additional remote computers 52 may also be used to visualize the results of the detection and length measurements of single molecules in the sample 12. The remote computers 52 may include personal computers (PCs), laptops, tablet computing devices, and the like. In this regard, results may be shared with multiple different users beyond the mobile phone 100 that is used to run the test. Note that in an alternative embodiment, the images 50 do not need to be transferred to a second or remote computer 42. Rather, the processor (or multiple processors) contained within the mobile phone 100 may process the images and analyze the results. In such an embodiment, there is no need to off-load or transfer images to a remote server 42 or the like.

Figure 2:
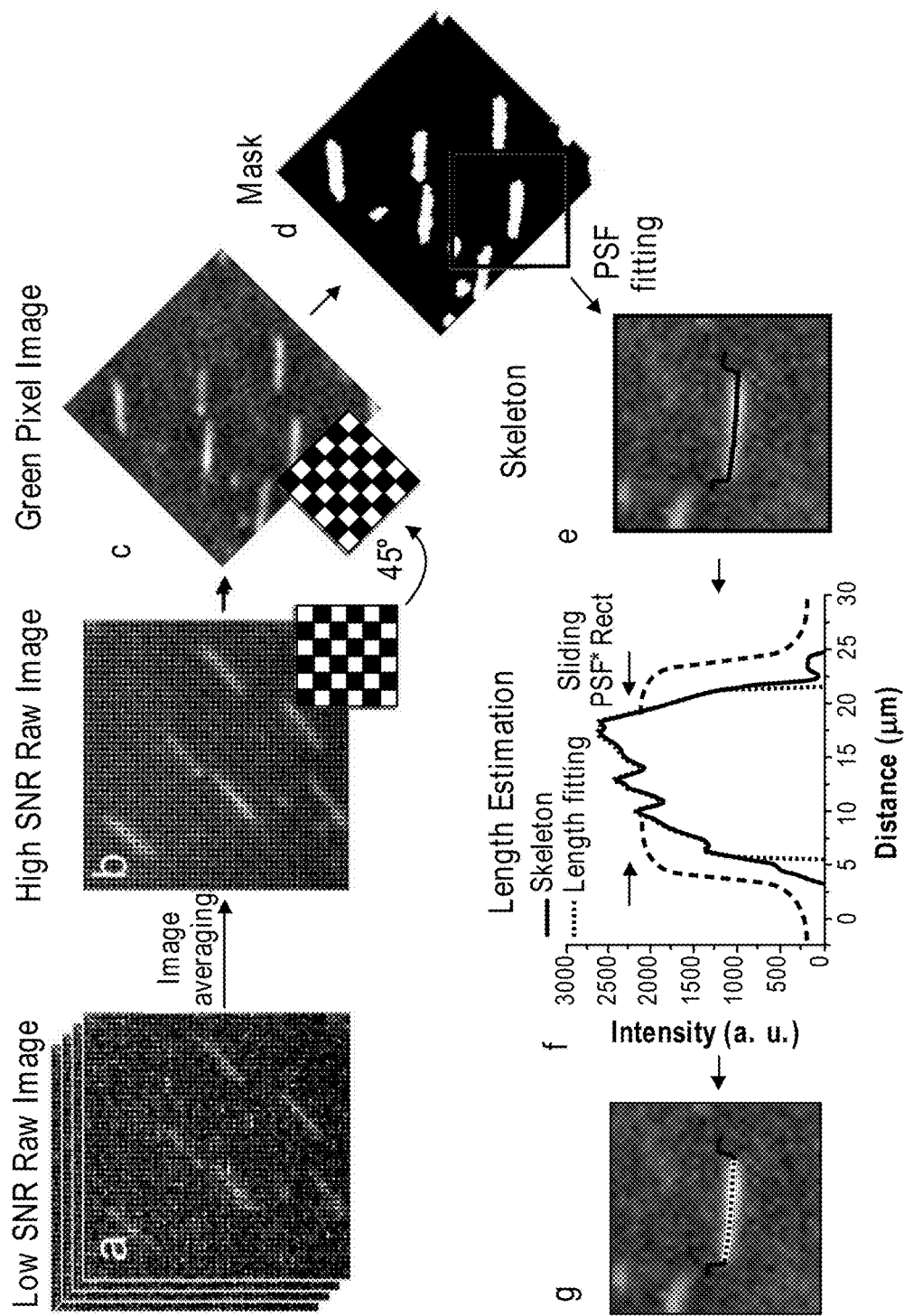
FIG. 2 illustrates a flow chart illustrating the operations used to automatically determine the length of single molecules (e.g., nucleic acid) by image processing software contained in the remote computer of FIG. 1E (or mobile phone in other embodiments).
Figure 8A:
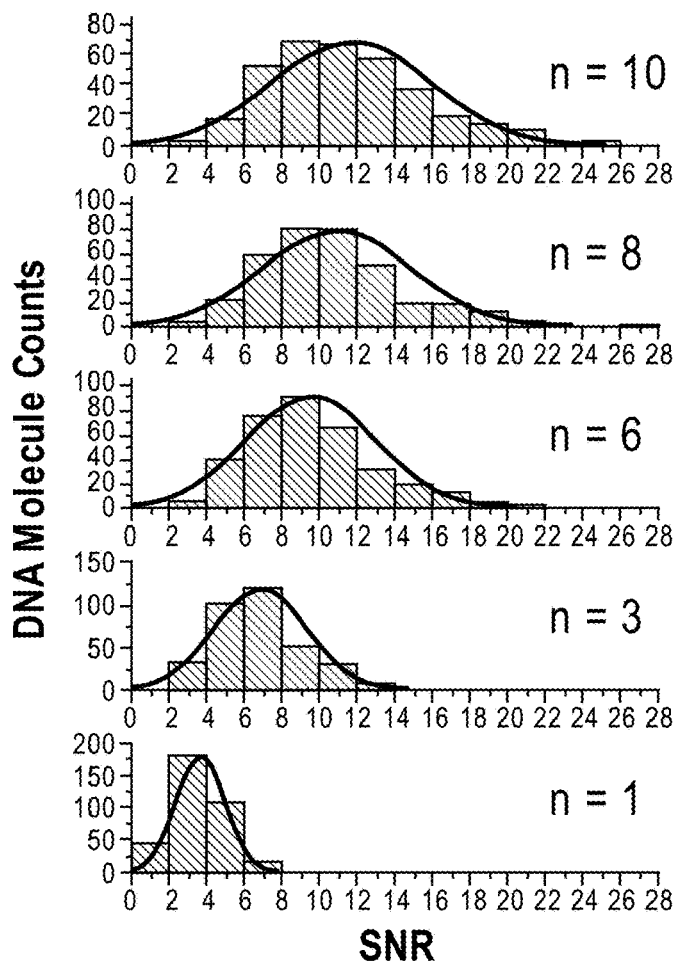
FIG. 8A illustrates quantitative SNR analysis of single DNA molecules as a function of the number of mobile phone image frames (n) for image averaging with n=1, 3, 6, 8, and 10. The solid lines are fitted normal distribution functions based on measured histograms.
Figure 8B:
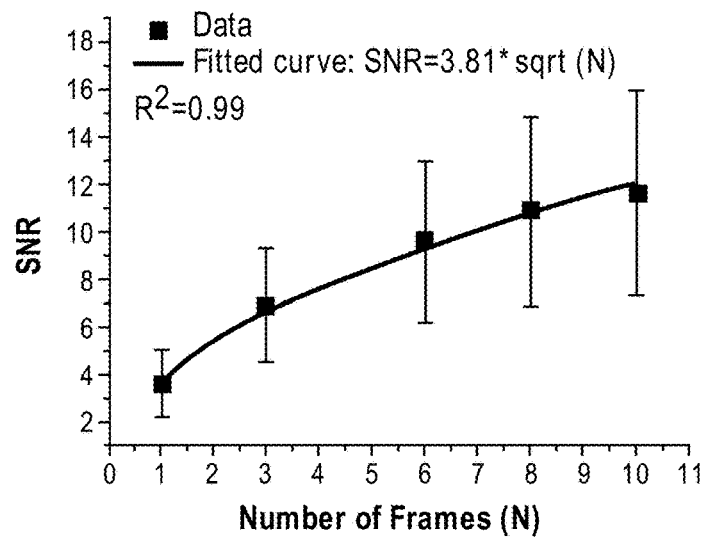
FIG. 8B is a graph of SNR as a function of the number of mobile phone image frames (n). The mean SNR of the single DNA images improves proportional to proportional to $\sqrt{n}$.
Figure 10:
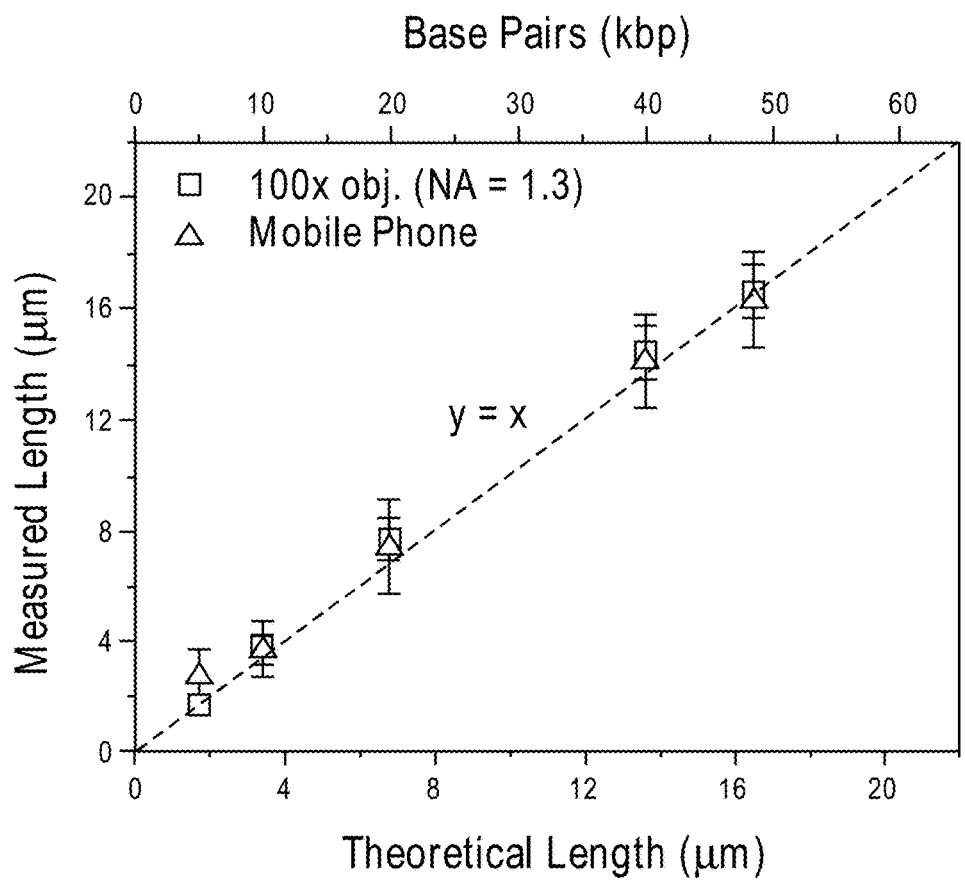
FIG. 10 illustrates a graph of the mean DNA lengths measured by the mobile phone (triangles) and the bench-top fluorescence microscope. The theoretical length of the fully stretched DNA molecule was calculated based on 0.34 nm per base pair. The full length of the error bar for each data point represents twice the standard deviation of a normal distribution curve that is fitted to the measured DNA length histograms shown in FIGS. 7A-7E.

FIG. 2 illustrates a flow chart illustrating the operations used to automatically determine the length of single molecules (e.g., nucleic acid) using the image processing software 46 contained in the remote computer 42 of FIG. 1E. To measure the lengths of individual molecules imaged on the mobile phones 100 using the modular attachment devices 10, the algorithm illustrated in FIG. 2 is used to process images 50 (operation a in FIG. 2). This automated length estimation process starts with digital alignment of multiple images 50 and then averaging (operation b) of multiple fluorescence images 50 recorded on the mobile phone 100 using the lossless digital negative (DNG) format, which displays the image in a Bayer pattern without any demosaicing and compression steps. This averaging operation significantly improves the SNR of the images 50. For example, the mean SNR of single DNA molecules that were imaged in experiments (calculated for over >350 individual DNA strands) increased from 3.8 for a single frame to an SNR of 12.1 for an average of 10 frames (see FIGS. 8A and 8B), following an SNR improvement factor that is proportional to the square root of the number of frames (n). In the experiments, 10-15 successive frames were averaged to benefit from this SNR improvement before the effects of photobleaching were observed.

The next operation (operation c in FIG. 2) in the length estimation algorithm involves rejection of all the blue and red pixels in the Bayer pattern such that only the green pixels of the image are kept, improving the spectral overlap with the fluorescent signal band. The resulting green pixel array is then rotated by 45 degrees to form a new image where the pixel period is "effectively" increased by $\sqrt{2}$ compared to the raw image pixel pitch; this is entirely due to the fact that red and blue pixels of the raw Bayer pattern are not used in the analysis. In some alternative embodiments, one or two colors of pixels remain (e.g., red or blue) and it does not have to be the green pixels as illustrated. In this particular embodiment, the dye that was used with the nucleic acid emitted light in the green color region. Other dyes or stains are possible that emit light in another color (e.g., red or blue). For example, if only the red or blue channels are used, there is no need for rotation of the image array. That is to say, the rotation of the image in operation c is not needed. The next operation (operation d) is the generation of a binary object mask for each molecule; which is automatically implemented by using a curvature detection algorithm to isolate the junctions of overlapping regions/masks due to closely located DNA molecules, significantly improving the overall detection efficiency of DNA strands. FIG. 9A illustrates a representative mobile phone fluorescence image of λ DNA displayed in RGB color scale. FIG. 9B illustrates a preliminary object mask generated by using an intensity threshold. FIG. 9C illustrates an improved masking method that utilizes a curvature detection algorithm to digitally separate end-to-end conjugated DNA masks (darker arrows) or side-by-side conjugated DNA masks (lighter arrows).

The next operation (operation d) of the algorithm is to establish the skeleton of each nucleic molecule through PSF fitting. The PSF of the mobile phone based microscope was previously estimated by averaging the two-dimensional (2D) intensity profiles of 100 nm fluorescent particles (e.g., beads) imaged on the same mobile phone 100. Obtaining the PSF of the mobile phone-based microscope needs to be done only once for each device. The PSF fitting procedure is initially applied to the short axis of each nucleic molecule to find its center. Note that this fitting process cannot be as accurate as determining the lateral position of a single fluorescent molecule because: (1) the PSF is estimated using 100 nm particles, and (2) there are more than one fluorescent molecule along the short-axis of each DNA strand; however this does not pose a limitation for the current mobile microscopy design and would be important to consider only for platforms that can achieve much smaller sizing accuracy and precision. The peak points of these centers are connected to form a DNA skeleton along the long axis direction. The next operation (operation e) is to find the edges of the DNA strand along its long axis by comparing a PSF-based theoretical edge intensity profile (dashed line in FIG. 2), which is calculated by using one-dimensional convolution of the mobile phone PSF with an ideal rectangular function with the measured intensity profile of the mobile phone image 50. The PSF-based edge function is digitally moved or slid (sliding PSF in FIG. 2) on the nucleic acid skeleton toward both of its ends until a minimum difference between the theoretical and the actual edge functions is observed. The estimated length of the stretched nucleic molecule is then indicated by a curve that connects both of these end points through the calculated skeleton. Operation g in FIG. 2 illustrates a line for the estimated length of the nucleic acid that is superimposed on the calculated nucleic acid skeleton. The line is truncated as compared to the skeleton line formed in operation e due to the minimization process performed using the measured edge intensity and sliding PSF edge function as explained above. For extremely low SNR DNA molecules, where these PSF fitting procedures cannot be successfully applied, the length of the molecule can also be estimated by thresholding the measured DNA intensity profile.

Figures 3D, 3E, 3F:
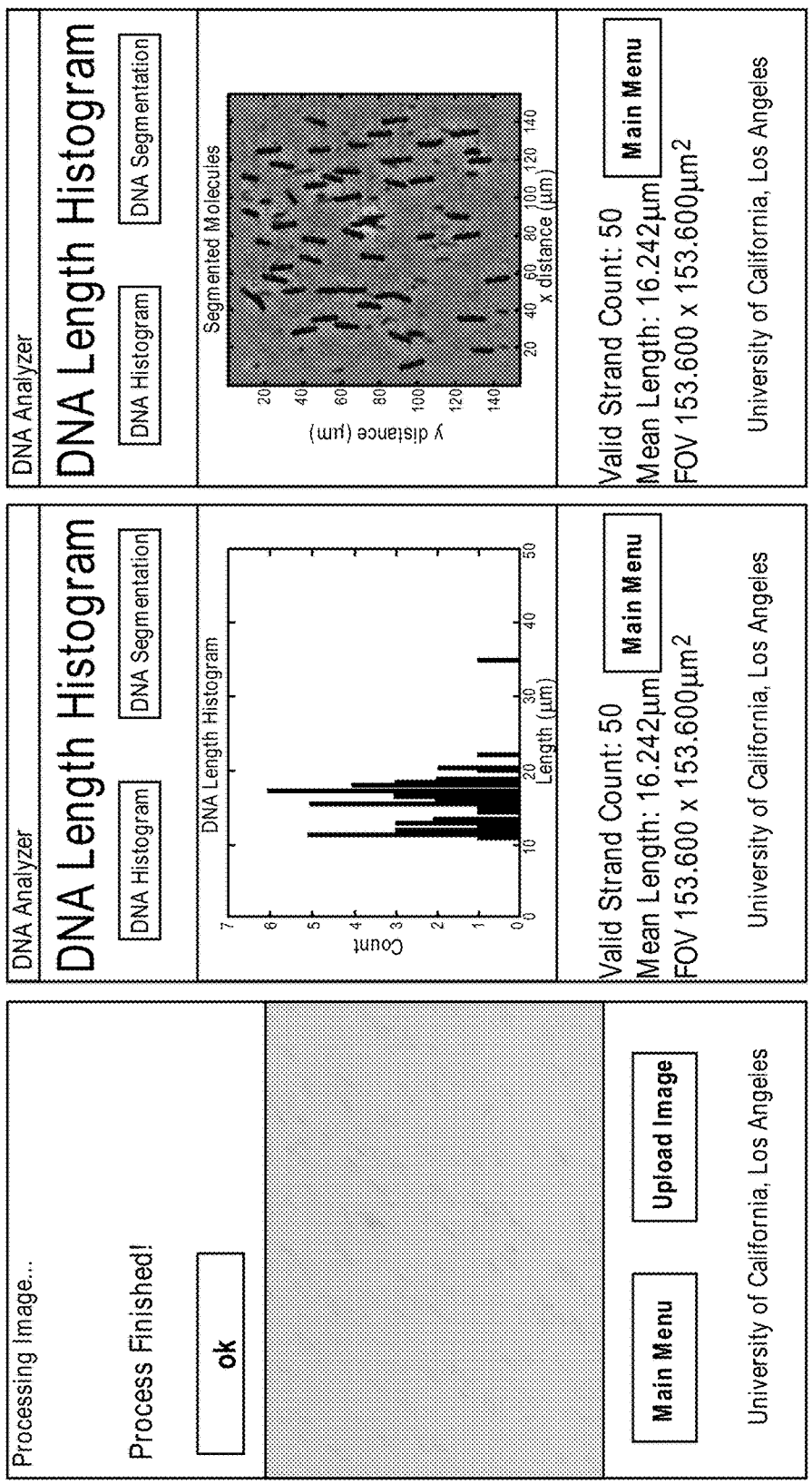

FIGS. 3A-3F illustrate screenshot images illustrating the GUI of the software application 106 running on the mobile phone 100 that is used to acquire images and upload the same to a remote computer 42 for processing and analysis. Results are returned to the mobile phone where they are displayed to the user on the GUI. FIG. 3A illustrates the main menu of the software or application 106. In this specific embodiment, the software is used to analyze DNA, although it should be understood that other molecules besides nucleic acids can be visualized using this platform. In the main menu, the user is given the option of capturing an image by running a current test or experiment or selecting a previously obtained image (e.g., from a prior test or experiment). The user also has the option of seeing the history details of prior tests that have been run on the microscope platform. FIG. 3B illustrates a screen shot of a captured or selected fluorescent image that was obtained with the microscope platform. The user is given the option to upload the image to the remote computer 42. FIG. 3C illustrates the GUI displaying to the user that the image is being uploaded and processed by the remote computer 42. FIG. 3D illustrates a notice to is presented to the user to notify the user that image processing has ended. FIG. 3E illustrates a histogram showing the measured lengths of DNA in a sample from a 153.6×153.6 μm² FOV. The user is also presented with a strand count (in this example 50) as well as a mean length (in this example 16.242 μm). FIG. 3F illustrates a labelled fluorescence image of DNA segmentation that shows each measured DNA molecule.

EXPERIMENTAL

Methods

Design of Mobile Phone-Integrated Fluorescence Microscopy.

A field-portable, mobile phone-based fluorescence microscope was created by integrating a 3D printed modular attachment device to the existing camera housing of a smartphone (Lumia 1020, Nokia). This robust mobile phone attachment was designed in Autodesk Inventor and printed by using a 3D printer (Dimension Elite 3D). A 450 nm laser diode powered by three AAA batteries and a constant current output driver was used as the excitation light, which illuminated the sample at an incidence angle of ~75°. The laser beam was focused through a small convex lens (f=35 mm) to form a tight illumination spot. The average illumination power density at the sample plane was estimated to be 2.4 W/cm². To dissipate the heat, the laser diode was mounted on a Φ12×30 mm copper host and further surrounded by a Φ18×40 mm aluminum heat sink. The focus of the mobile phone microscope was controlled by a miniature dovetail stage (DT12, Thorlabs) which moved both the sample chamber and the light source. The fluorescence signal emitted from the specimen was collected though an external lens (f=4 mm) in addition to the built-in mobile phone camera lens (f=6.5 mm), and finally recorded by the mobile phone CMOS sensor chip (pixel pitch: 1.12 μm; image size: 7152×5368 pixels). Two stacked 500 nm longpass filters (FF01-500/LP-23.3-D, Semrock) were placed between the external lens and the mobile phone camera lens to reject the scattered background light due to high-power laser excitation.

Fluorescence Labeling and Stretching of DNA Molecules.

Lambda DNA (48,502 b.p., Life Technologies) and T7 DNA (39,937 b.p., Boca Scientific Inc.) were labeled with an intercalating dye YOYO-1 (Excitation/Emission=491/509 nm, Life Technologies) at a base pair to dye molecule ratio of 5:1 following a standard labeling protocol. Both λ and T7 DNA and YOYO-1 were diluted with 1×TAE buffer (40 mM Tris-acetate, 1 mM EDTA, pH 8.3, Life Technologies) to desired concentrations in low-retention DNA tubes (LoBind, Eppendorf). 32 μL of 10 ng/μL DNA was pipetted gently and added into 480 μL of 200 nM YOYO-1 solution. The mixture was incubated for 1 hour at room temperature covered by aluminum foil. The stained DNA solutions (0.6 ng/μL) were stored at 4° C. for future use and stable for at least several weeks.

Before stretching of DNA molecules, prestained DNA solutions were warmed up at 65° C. for 10 minutes, followed by a quick cooling in running water for 2 minutes to open up the sticky ends of DNA. Then, 5 μL of this pre-labeled DNA solution was diluted in 110 μL imaging buffer (1×TAE buffer added with 4.8% (v/v) 2-mercaptoethonal and 500 nm green fluorescent beads) to a final concentration of ~0.03 ng/μL.

Preparation of Substrates for DNA Stretching:

The DNA stretching substrates were prepared by functionalization of glass coverslips with a mixed layer of silane molecules, which consisted of (3-aminopropyl) triethoxysilane (APTES, Sigma) and allyltrimethoxysilane (ATMS, Sigma). Standard 22×22 mm coverslips (Fisherbrand) were first rinsed with acetone, isopropanol, methanol, and deionized (DI) water. After air-blow drying, both sides of coverslips were treated with plasma (BD-10AS, Electro-Technic Products, Inc.) for 10 seconds to activate the glass surface with hydroxyl groups. The plasma-treated coverslips were then immersed into a mixture silane solution in acetone (1% APTES, 1% ATMS, v/v) and coated for 10 minutes. The coated coverslips were thoroughly rinsed with acetone and de-ionized (DI) water, and then dried by blown air.

To stretch DNA molecules, the 22×22 mm silanized coverslip was placed on a solid planar surface, and 3 μL of the stained DNA solution diluted in imaging buffer was pipetted onto the center of the coverslip. Another 18×18 mm plasma-treated coverslip was held horizontally which was approximately 1 mm above the bottom coverslip. The top coverslip was then quickly pressed down toward the bottom substrate with a tweezer. The droplet containing the DNA samples was pushed from the center to the edges between the top and bottom coverslips, forming a strong shearing flow, which stretches the DNA molecules on the bottom substrate. The sample was then sealed with colorless nail polish and imaged using the microscopes described herein.

Image Acquisition.

The DNA sample of interest, after the preparation steps detailed earlier, was loaded onto the sample holder and inserted into the mobile phone attachment. All the fluorescence images were recorded in a lossless raw format (DNG) with an integration time of ~4 seconds per frame. About 10-15 frames of the same DNA sample were captured for image averaging, before photobleaching was observed.

Imaging of DNA Molecules on a Conventional Bench-Top Microscope:

Glass coverslips with stretched DNA molecules were imaged, for comparison purposes, on an Olympus IX73 inverted microscope with a UPIanFLN 100× (NA=1.30) oil-immersion objective lens. Samples were excited by a 100 W mercury lamp. Fluorescence images were recorded by a passively cooled monochrome CCD camera (QIClick, QImaging) in 12-bit Tiff format.

Windows® Based Smart Mobile Application Development.

A custom-developed Windows® mobile phone application was developed that allows for analysis of the lengths of single DNA molecules imaged on the phone. This application can be used to capture an image of the sample or alternatively open a saved image for DNA length measurement. The selected or captured image is subsequently uploaded to a remote server through HTTP for rapid digital processing. On this server, the uploaded image is first converted from DNG format to 16-bit TIFF format and then processed in MATLAB using the length quantification method described previously. It should be understood that the image processing algorithm may be programmed using any number of computer programs. Once the processing is finished, the results (a histogram of DNA length measurements and a corresponding labeled image marking all the locations of analyzed DNA molecules) are then sent back to the originating mobile phone. The processing time for a 200×200 pixel cropped section of the full field-of-view is ~7 seconds in MATLAB using a single PC (CPU: Intel Xeon ES-2620), and it can be reduced by more than an order of magnitude if the same algorithms are implemented in a more efficient software language such as C/C++ and/or adapted to utilize GPUs. Depending on the network speed, the upload time of the 41 megapixel raw DNG image varies between 10 seconds to 3 minutes.

Object Mask Generation to Separate Closely Located DNA Molecules:

A curvature detection algorithm was implemented in the masking method to detect connecting masks from closely located molecules and eventually separate those masks into single masks. The algorithm first smooths the edges of the preliminary object mask that is generated by intensity thresholding with a median filter. Then it automatically recognizes two different types of DNA mask junctions: end-to-end and side-by-side using the overall differences in object width in these two scenarios as seen in FIG. 9C. For end-to-end DNA junctions, the first derivatives of the mask curvatures along both sides of the long axis of the DNA were calculated to find the peak points. These two peak points were then connected to separate the end-to-end DNA mask (FIG. 9C, darker arrows). For side-by-side DNA junctions, two starting points in the junction area were defined by detecting the number of y coordinates (2 for single objects, 3 for junction points, and 4 for two parallel objects) at each x position. After determining these two starting points, a tracking algorithm was applied to form a continuous separation line between the molecules (FIG. 9C, lighter arrows).

DNA Gel Electrophoresis Experiments:

0.6% Agarose gel was prepared with 1×TBE (Tris/Borate/EDTA) buffer and 0.5 µg/ml of ethidium bromide was added for DNA detection under UV illumination. Two samples, 500 ng of λ DNA and T7 DNA, were loaded into the sample wells. For comparison, 1 µg of HindIII digested λ DNA and 1 kb DNA ladder were also loaded on the gel as markers. The gel was run at 40V for 8 hours before imaging.

Results and Discussion

In the experiments, mechanical stretching of DNA molecules from coiled form into a linear shape was achieved by quickly compressing a droplet of stained DNA solution (3 µL) in between two coverslips to generate a transient fluid flow. This procedure stretches the DNA fragments by utilizing the strong shear force that is created at the silanized bottom glass substrate. FIG. 4A illustrates a large field-of-view (FOV) (~2 mm$^2$) mobile phone image of fluorescently labeled DNA molecules stretched on a glass substrate alongside corresponding images obtained with bench-top microscope having a 100× oil-immersion objective lens (Numerical Aperture, NA=1.3) and a cooled monochrome CCD camera. The region of high-quality DNA stretching surrounds the initial droplet position and forms a ring-shaped band with its width spanning over a few millimeters, which provides a sufficient sample area for imaging of DNA molecules using the mobile phone attachment with a large FOV of ~2 mm$^2$.

To test single molecule DNA imaging performance of the mobile phone microscope, a double-stranded λ bacteriophage DNA (~48 kbp) was used. The sample glass substrate with combed DNA molecules of interest was placed within the sample holder and inserted into the modular attachment device that was secured to the mobile phone. Image acquisition for each sample was repeated 10-15 times for the same region of interest with an exposure time of ~4 seconds per frame; these multiple frames were then averaged to create the final raw fluorescence image of the sample. FIG. 4A displays one of these fluorescence images captured on the mobile phone device, showing that λ DNA molecules are linearly stretched around the initial droplet position and that the DNA alignment direction is approximately perpendicular to the boundary of the droplet. The mobile phone image in FIG. 4A covers a large FOV of 1.76 mm×1.09 mm, and this is especially advantageous for high-throughput imaging and sizing of a large number of DNA molecules within the same sample. FIGS. 4B, 4D, 4F show selected magnified regions that are denoted with the rectangles in FIG. 4A, which clearly illustrate that the single DNA strands imaged on the mobile phone attachment exhibit a comparable contrast to the images of the same molecules obtained using a 100× oil-immersion objective lens (NA=1.30) and a passively cooled monochrome CCD camera on a conventional bench-top fluorescence microscope (FIGS. 4C, 4E, 4G).

Figure 5A:
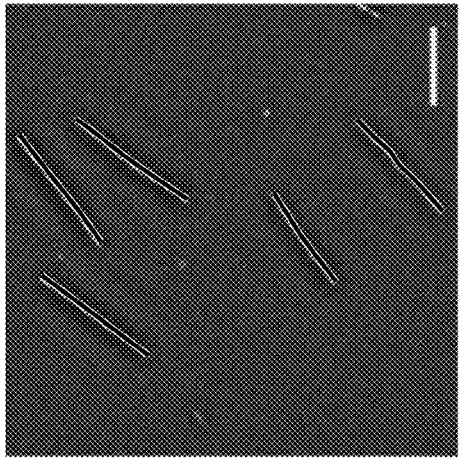
FIG. 5A illustrates an image of single λ DNA molecules imaged by the mobile phone-based imaging device. Lines that are superimposed in each image denote the automatically determined length measurements for each DNA strand. Scale bar=10 µm.
Figure 5B:
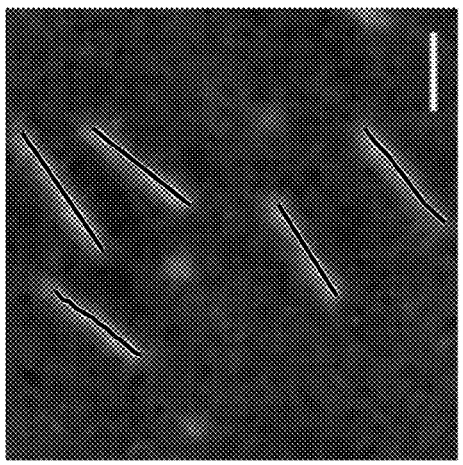
FIG. 5B illustrates an image of same single λ DNA molecules of FIG. 5A obtained with a conventional bench-top microscope (100× oil-immersion objective-lens, 1.3 NA).
Figure 5C:
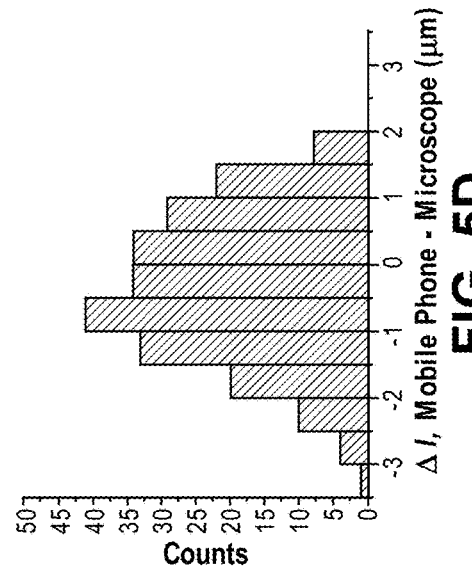
FIG. 5C illustrates a scatter plot of DNA length measurement obtained by the mobile phone device plotted against the bench-top microscope results. The solid line is a linear fit to the raw data.
Figure 5D:
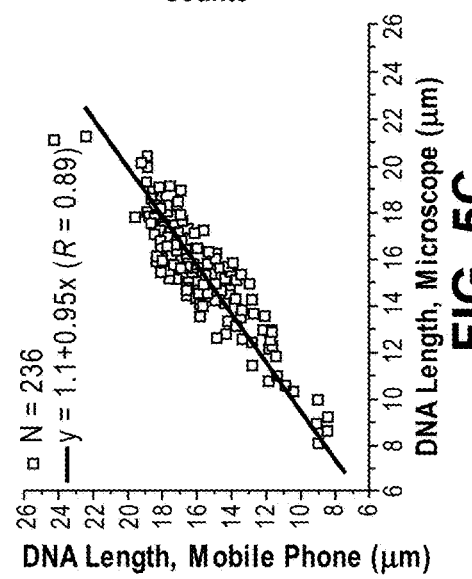
FIG. 5D illustrates a histogram of the distribution of the length measurement differences (Δl) between mobile phone results and conventional microscope results, where the mean error is −0.33 μm and the standard deviation is 1.08 μm.

To measure the respective lengths of the individual DNA molecules imaged on the mobile phone based fluorescence microscopy platform, an algorithm was created as described previously with respect FIG. 2. To test the accuracy and precision of the mobile phone-based DNA length measurements, a conventional bench-top fluorescence microscope was used with a 100× oil-immersion objective lens (NA=1.3) and a passively cooled CCD camera as the reference method. FIGS. 5A and 5B illustrate, respectively, zoomed-in regions of the λ DNA sample imaged on the mobile phone platform and a conventional fluorescence microscope and each DNA molecule image is superimposed with a length profile (line) calculated using the computational procedures outlined earlier. As illustrated in FIG. 5C, DNA length values measured on the mobile phone platform are in good agreement with those obtained using the bench-top fluorescence microscope. The mean error for the mobile phone based length measurement results is ~0.33 µm or ~0.96 kbp (shorter) compared to bench-top microscope measurements, with a standard deviation of ~1.08 µm or ~3.17 kbp (FIG. 5D).

Experiments were also conducted for differentiating different DNA sequences that are combed, imaged, and measured under the same imaging conditions by using the mobile phone microscopy platform. In these experiments, relatively large molecular weight DNA strands were selected, corresponding to 48.5 kbp (λ DNA) and 39.9 kpb (T7 DNA), where conventional gel electrophoresis methods would not be able to differentiate as well as three shorter DNA fragments (5, 10, and 10 kbp) to demonstrate a broad sizing range.

FIGS. 6A-6E illustrate respective images of these single DNA molecules with various lengths imaged by the mobile phone microscopy platform (top row) along with images obtained from a bench-top inverted fluorescence microscope equipped with a 100× objective lens (NA=1.3) and a cooled monochrome CCD camera (bottom row). FIGS. 7A-7E illustrate the length distributions of these different DNA samples quantified by the mobile phone microscopy platform (top row) as well as the conventional fluorescence microscope (bottom row).

The measured number of DNA molecules (N) is significantly less in bench-top microscope measurements compared to the mobile phone results due to much smaller FOV of the 100× objective lens. The average length (L) of the stretched λ DNA and T7 DNA molecules measured using the mobile phone device is 16.31 µm (FIG. 7E top histogram) and 14.10 µm (FIG. 7D top histogram), respectively, which are in good agreement with 16.64 µm and 14.41 µm that were measured using the conventional bench-top microscope, yielding an average length measurement accuracy of 98.0% and 97.8%, respectively. It should be emphasized that separation and detection of large molecular weight DNA segments are major challenges for conventional gel electrophoresis techniques which work better for small DNA fragments. Gel electrophoresis, for example, cannot distinguish between 48.5 kbp (λ DNA) and 39.9 kpb (T7 DNA). In contradistinction, the mobile phone based microscopy based single DNA imaging approach described herein exhibits better differentiation resolution, especially for large DNA molecules compared to gel electrophoresis methods. Therefore, the mobile phone imaging platform provides a cost-effective, compact and light-weight solution for quantitative characterization and differentiation of single DNA fragments even in field and resource limited settings.

Figures 7D, 7E:
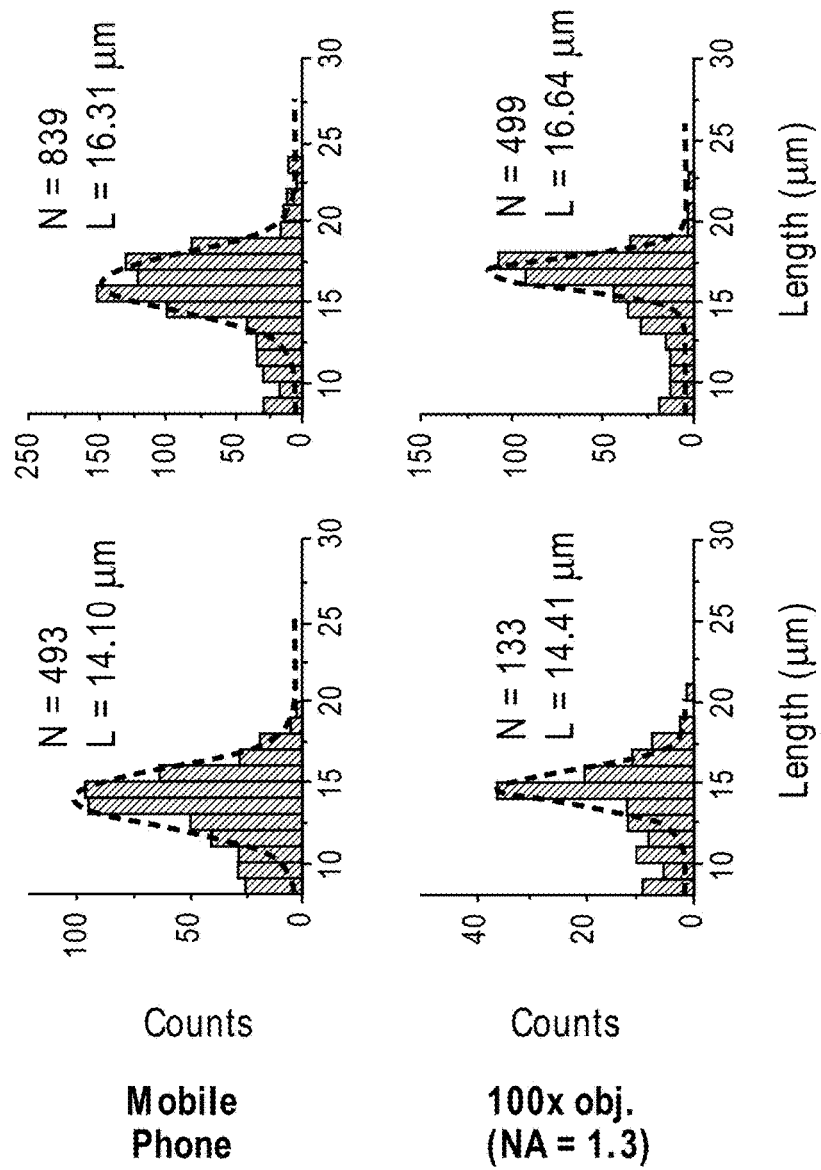
FIG. 7D illustrates a histogram of measured lengths for a 40 kbp segment of T7 DNA using the mobile phone based microscope platform (top) along with histogram measurements obtained using a bench-top fluorescence microscope (NA=1.3) (bottom).
FIG. 7E illustrates a histogram of measured lengths for a 48 kbp segment of λ DNA using the mobile phone based microscope platform (top) along with histogram measurements obtained using a bench-top fluorescence microscope (NA=1.3) (bottom).

There also was good agreement in the measurement for shorter DNA fragments (20 and 10 kbp) as illustrated in FIG. 7B and FIG. 7C, yielding an average length measurement accuracy of 96.4% and 96.9% for 20 kbp and 10 kbp DNA samples, respectively, compared to the benchtop microscope measurements. These results, as summarized in FIGS. 7B-7E and FIG. 10, illustrate that for 10 kbp and longer DNA molecules the mobile-phone platform can achieve an average DNA sizing accuracy of <0.34 μm or <1 kbp. On the other hand, for 5 kbp DNA samples, the average length measured by the mobile-phone based imaging platform was considerably longer compared to the bench-top microscope measurement results as illustrated in FIG. 7A (L=2.76 μm vs. L=1.66 μm, respectively). This length measurement discrepancy for 5 kbp DNA samples can be attributed to the reduced detection SNR for such short DNA fragments as well as to the limited spatial resolution of the mobile-phone, both of which can be substantially improved by e.g., substituting the current external lens in the imaging design with a higher numerical aperture lens.

This simple, field-portable, and cost-effective fluorescent microscopy platform that can be installed on a mobile phone permits direct visualization of individual nucleic acid (e.g., DNA) molecules that are fluorescently labeled over a large FOV of ~2 mm². A robust image processing framework that is integrated with remote processing was also developed to overcome the SNR challenge and allow quantitative length measurements of single DNA molecules imaged on the mobile phone platform, achieving a length accuracy of ~0.96 kbp and a standard deviation of ~3.17 kbp when compared to the results of a bench-top fluorescence microscope. High-throughput imaging, length quantification, and differentiation of individual λ and T7 bacteriophage DNA molecules are also demonstrated using the same mobile phone based microscope. Further improvements in the image quality and sizing accuracy can also be achieved by using specially designed substrates, including for example plasmonic designs, to significantly increase the fluorescent signal of each molecule through field enhancements. This mobile DNA imaging and sizing platform can be quite useful in various biomedical applications including for example field and POC measurements of copy number variations (CNVs), which might relate to e.g., early detection of cancers, nervous system disorders, and drug resistance in infectious diseases, among many others. For example, certain cancers and genetic disorders can be diagnosed or identified based on the number of copies of a particular gene or DNA sequence. The mobile phone based imaging platform described herein may be used to identify samples having particular copy numbers based on the length of the detected DNA sequences. For instance, a gene segment of DNA with three (3) copy numbers of a particular gene may appear three times as large as another sample with only a single copy of the gene. This difference can be distinguished using the microscope platform described herein. For such uses, a nucleic sample may be digested by one or more enzymes to cut the DNA in appropriate locations. The digested DNA may be fluorescently labeled and then subject to imaging and analysis as described herein.

While embodiments of the present invention have been shown and described, various modifications may be made without departing from the scope of the present invention. For example, features or aspects of one embodiment may be incorporated in other embodiments even if not specifically identified as being substitutable. In addition, while certain embodiments have focused on using green colored fluorescent light for imaging of nucleic acids, other colored dyes or stains may also be used. The following publication, Wei et al., Imaging and Sizing of Single DNA Molecules on a Mobile Phone, ACS Nano, Vol. 8, No. 12, pp. 12725-12733 (Dec. 10, 2014) is incorporated by reference as if set forth fully herein. The invention, therefore, should not be limited, except to the following claims, and their equivalents.

What is claimed is:

1. A device for imaging fluorescently labeled nucleic acid molecules in a sample comprising:
   a mobile phone having a camera therein;
   a modular attachment device configured to mount to the mobile phone and position a fluorescently labeled nucleic acid sample contained therein within a field of view of the camera, the modular attachment device comprising:
      an excitation light source;
      a sample holder configured to hold the sample containing the fluorescently labeled nucleic acid compressed between two optically transparent substrates, wherein fluorescently labeled nucleic acid molecules are stretched or extended in response to a compression force applied to the two optically transparent substrates;
      a lens or set of lenses for magnifying the image of the sample;
      a filter interposed between the lens and the camera of the mobile phone and configured to reject scattered background light from the excitation light source and transmit fluorescent light through the filter;
      a moveable stage for moving the excitation light source and sample holder relative to the camera of the mobile phone; and
   wherein the mobile phone comprises software executed thereon to identify molecules of fluorescently labeled nucleic acid in the sample along with their respective lengths or lengths of sub-regions of the nucleic acid molecules.

2. The device of claim 1, wherein the mobile phone comprises at least one processor configured to transmit one or more images obtained from the mobile phone camera to a remote or local computer for image processing and analysis, the mobile phone configured to receive analysis results from the remote computer including the length of nucleic acid molecules in the sample.

3. The device of claim 1, wherein the mobile phone comprises at least one processor configured for processing images obtained of the sample with the mobile phone and output an analysis of the sample including the length of nucleic acid molecules in the sample or specific sub-regions of nucleic acid molecules.

4. The device of claim 1, wherein the sample holder comprises first and second optically transparent substrates and the sample of interest is interposed there between.

5. The device of claim 1, wherein the excitation light source comprises at least one of a laser diode, light emitting diode, or an array of the same.

6. The device of claim 2, wherein the mobile phone transmits a plurality of images to the remote or local computer, wherein the remote computer subjects the plurality of images to image averaging to form a higher SNR image.

7. The device of claim 6, wherein the remote or local computer processes the higher SNR image to retain one or two colors of pixels from the higher SNR image.

8. The device of claim 7, wherein the remote or local computer rotates the retained pixels in the image by about 45 degrees.

9. The device of claim 8, wherein the remote computer generates an object mask of the molecules of fluorescently labeled nucleic acid in the rotated image.

10. The device of claim 9, wherein the remote computer generates a line or skeleton of the fluorescently labeled nucleic acid molecules or a specific sub-region of the nucleic acid molecules through fitting a function that estimates or mimics the point spread function (PSF) of the mobile phone camera.

11. The device of claim 10, wherein the remote computer generates a length measurement for the fluorescently labeled nucleic acid molecules or a specific sub-region of nucleic acid molecules based on the PSF fitting.

* * * * *